United States Patent
Chan et al.

(10) Patent No.: US 9,879,224 B2
(45) Date of Patent: Jan. 30, 2018

(54) LABEL-FREE IDENTIFICATION OF STEM CELL-DIFFERENTIATED CELLS

(71) Applicant: The Regents of the University of California, Oakland, CA (US)

(72) Inventors: James W. Chan, Davis, CA (US); Deborah Lieu, Davis, CA (US)

(73) Assignees: The Regents of the University of California, Oakland, CA (US); Lawrence Livermore National Security, LLC, Livermore, CA (US)

( * ) Notice: Subject to any disclaimer, the term of this patent is extended or adjusted under 35 U.S.C. 154(b) by 591 days.

(21) Appl. No.: 14/354,067

(22) PCT Filed: Oct. 26, 2012

(86) PCT No.: PCT/US2012/062141
§ 371 (c)(1),
(2) Date: Apr. 24, 2014

(87) PCT Pub. No.: WO2013/063406
PCT Pub. Date: May 2, 2013

(65) Prior Publication Data
US 2014/0273207 A1    Sep. 18, 2014

Related U.S. Application Data

(60) Provisional application No. 61/552,390, filed on Oct. 27, 2011.

(51) Int. Cl.

| | |
|---|---|
| *C12N 5/07* | (2010.01) |
| *C12N 5/10* | (2006.01) |
| *C12N 5/00* | (2006.01) |
| *C12N 5/02* | (2006.01) |
| *C12N 5/077* | (2010.01) |
| *G01N 21/63* | (2006.01) |
| *C12M 1/00* | (2006.01) |

(52) U.S. Cl.
CPC .......... *C12N 5/0657* (2013.01); *C12M 47/04* (2013.01); *G01N 21/636* (2013.01)

(58) Field of Classification Search
None
See application file for complete search history.

(56) References Cited

U.S. PATENT DOCUMENTS

2010/0241357 A1    9/2010  Chan et al.
2011/0027787 A1    2/2011  Chuck

OTHER PUBLICATIONS

Lee et al., Tiss. Eng., 12(10):2835-2841 (2006).*
Guo et al., J. Biomed. Opt., 13(5):050505-1-050505-3 (2008).*
Emmelkamp et al., Electrophoresis 25:3740-3745 (2004).*
van Laake et al., Cell. Mol. Life Sci., 67:277-290 (2010).*
Chu et al., Opt. Exp., 11(8):933-938 (2003).*
Awasthi et al., J. Biophotonics. 5(1):1-13 (2012).*
Celso et al., Nature Let., 457:92-96 (2009).*
Gherghiceanu et al., J. Cell. Mol. Med., 14(4):871-877 (2010).*
Rice e al., J. Biomed. Opt., 12(6):060504-1-060504-3 (2007).*
Stringari et al., J. Biomed.Opt., 17(4),046012-1-046012-11 (2012).*
Sung et al., Integr. Biol. Camb., 3(4): 439-450 (2011).*
Teng et al., Invest. Ophthal. Vis. Sci., 47(3):1216-1224 (2006).*
Chan, J.W. et al. (2009) "Label-free biochemical characterization of stem cells using vibrational spectroscopy," J. Biophoton., 2(11):656-668.
Uchugonova, A. et al. (2008) "Two-photon autofluorescence and second harmonic imaging of adult stem cells," Journal of Biomedical Optics, 13(5):054068-1-054068-8.
International Search Report (ISA/US) for International Application No. PCT/US2012/062141, dated Jan. 25, 2013, 2 pages.

* cited by examiner

*Primary Examiner* — Thomas J Visone
(74) *Attorney, Agent, or Firm* — Foley & Lardner LLP; Antoinette F. Konski

(57) ABSTRACT

Methods are disclosed for isolation of a stem-cell derived differentiated cell, which method entails illuminating an incident light onto a plurality of stem-cell derived cells that comprise at least an undifferentiated cell and a differentiated cell possessing a noncentrosymmetric structure, wherein the differentiated cell generates second-harmonic light from the incident light; and isolating the differentiated cell identified by the second-harmonic light. Devices for carrying out the methods are also provided.

16 Claims, 8 Drawing Sheets

LABEL-FREE IDENTIFICATION OF STEM CELL-DIFFERENTIATED CELLS

CROSS-REFERENCE TO RELATED APPLICATIONS

This application is a national stage application under 35 U.S.C. § 371 of International Application No. PCT/US2012/062141, filed Oct. 26, 2012, which in turn claims the benefit under 35 U.S.C. § 119(e) of U.S. Provisional Application No. 61/552,390, filed Oct. 27, 2011, the contents of each of which are incorporated by reference in their entirety into the current disclosure.

GOVERNMENT LICENSE RIGHTS

This invention was made with Government support under Grant No. PHY0120999, awarded by the National Science Foundation. The Government has certain rights in this invention.

BACKGROUND

Human embryonic and induced pluripotent stem cells (PSCs) are defined, in part, by their ability to differentiate into all cell types of the human body. For cardiovascular medicine, PSC-derived cardiomyocytes (PSC-CMs) have the potential to be an unlimited ex vivo source of transplantable cardiac cells for use in regenerative therapies of the heart. PSC-CMs can also be used for cardiac drug discovery and screening, and the development of in vitro models of various genetic heart diseases. These basic and clinical applications of PSC-CMs require the elimination of the undifferentiated cells and non-CMs to yield pure PSC-CM populations. For transplantation purposes, having a well-defined population of cardiomyocytes (CMs) may be critical to optimizing stem cell therapy. Even more critical is the removal of PSCs from PSC-CMs due to their tendency to form teratomas upon transplantation into a mature tissue environment. In vitro, a pure, countable population of CMs is necessary for well-controlled experimentation.

There is, however, currently no widely accepted, non-invasive method for purifying live PSC-CMs. The difficulty with PSC-CM purification lies in the fact that CMs have no established, highly specific surface markers that make their identification and physical separation feasible. They may be identified by immunostaining for intracellular cardiac-specific proteins, but at the cost of rendering the cells nonviable.

To date, a handful of approaches for selecting viable PSC-CMs from stem cells have been demonstrated, but each has its own shortcoming. The ectopic expression of a fluorescence reporter protein under the transcriptional control of a CM-specific promoter, achieved by lentiviral transduction, has been used to identify human embryonic stem cell (hESC) derived cardiomyocytes (hESC-CM) populations with >90% purity. However, the use of transgenic methods in patients raises clinical safety concerns that have not yet been resolved. Labeling with green fluorescent proteins has also been shown to affect actin-myosin interaction and impair the contractile activity of muscle. CMs may be selected based on physical size by means of a Percoll gradient, but purity is limited with this technique.

Yet another method selects cardiac progenitors using a cell surface protein (kinase-insert domain-containing receptor), but the progenitors selected still have the potential to differentiate into smooth muscle cells, cardiac fibroblasts and vascular endothelial cells. A more recent non-genetic approach that identifies live PSC-CMs by using a fluorescent dye to detect the increased mitochondrial content of PSC-CMs relative to PSCs and non-CMs has the potential to identify CMs with high specificity. However, the number of CMs isolated by mitochondrial staining was reported to be 60-90% of the number defined by α-actinin staining, suggesting that the method may not be sufficiently sensitive—it may be limited in its ability to identify less mature CM phenotypes. Furthermore, the use of dyes requires additional sample preparation steps that may lead to cell loss and raises potential toxicity issues for cell transplantation.

SUMMARY

Methods for isolation of a stem-cell derived differentiated cell are provided by this disclosure. The methods comprise, or alternatively consist essentially of, or yet further consist of, illuminating an incident light onto a plurality of stem-cell derived cells that comprise, or alternatively consist essentially of, or yet further consist of, at least an undifferentiated cell and a differentiated cell possessing a noncentrosymmetric structure, wherein the differentiated cell generates second-harmonic light from the incident light; and isolating the differentiated cell identified by detecting of the second-harmonic light generated by the cell. For the purpose of illustration only, the noncentrosymmetric structure is selected from the group of myosin, collagen, microtubule, axon or dendrite.

In the above methods, the differentiated cell is differentiated, in vitro, from a stem cell wherein the duration of the differentiation is less than 180 days or alternatively from about 180 days to about 3 days, or alternatively from about 180 days to about 30 days, or alternatively from about 30 days to about 0.5 days, or alternatively from about 30 days to about 1 day, or alternatively from about 30 days to about 2 days, or alternatively from about 30 days to about 5 days.

The methods are useful to isolate a differentiated cell from, for example, an immature cardiomyocyte, an immature skeleton muscle cell, an immature smooth muscle cell or an immature neuron that may be present in a heterogeneous population of cells. The heterogeneous population of cells may be of different phenoyptes or different stages of maturation, e.g., immature and mature. In one specific aspect, the differentiated cell is an immature cardiomyocyte.

The methods can be practiced on a stem cell such as for example, an embryonic stem cell, an induced pluripotent stem cell, a multipotent stem cell, an oligopotent stem cell or a unipotent stem cell.

In a further aspect, the incident light has a wavelength from about 700 nm to about 1500 nm. In another aspect, the incident light comprises pulses having a width of about 70 fs to about 10 ps. In a yet further aspect, the incident light has a repetition rate from about 1 KHz to about 100 MHz.

The method is useful in one aspect, in that the cell or cells is/are isolated in the absence of exogenous label or prior genetic modification of the cells. Non-limiting examples of exogenous labels include fluorescent labels or radioactive labels.

In a further aspect, the methods further comprise, or alternatively consist essentially of, or yet further consist of, suspending the cells in a medium prior to illuminating the incident light onto the cells, e.g., a medium that comprises collagenase. In a further aspect the medium does not contain trypsin. In another aspect, the medium contains collagenase but not trypsin.

The population of cells isolated by the methods are further provided. In one aspect, the population is a substantially homogenous population of cells of any one phenotype, e.g., a cardiomyoctye, a striated muscle cell, a smooth muscle cell, a neuron, a hematopoietic cell or a cartilage cell.

The method can be practiced on a stem cell of any species, e.g., a mammalian stem cell. Non-limiting examples are discussed infra and include a murine stem cell or a human stem cell.

This disclosure also provides a method of isolating cells, the method comprising, or alternatively consisting essentially of, or yet further consisting of, passing a plurality of cells through a device comprising, or alternatively consisting essentially of, or yet further consisting of: (a) a laser light source to cast an incident light on the cells and (b) a sensor configured to collect or detect second-harmonic light generated from the incident light, wherein the cells comprise at least an undifferentiated stem cell and a differentiated cell comprising a noncentrosymmetric structure; identifying the differentiated cell by the second-harmonic light generated on the cell; and collecting the differentiated cell.

In another aspect, a method of distinguishing two cells of different differentiation or maturation stages is provided. The method comprises, or alternatively consists essentially of, or yet further consists of, culturing or growing one or more stem cells under conditions to allow the stem cells to differentiate to at least two differentiated cells at different differentiation stages, at least one of which comprises a noncentrosymmetric structure; illuminating an incident light on the differentiated cells; and distinguishing the two differentiated cells by examining second-harmonic light generated on at least one of the two differentiated cells. In one aspect, second-harmonic light generated on the at least one of the two differentiated cells is examined by determining the intensity of the second harmonic light.

The population of cells isolated by the methods are further provided. In one aspect, the population is a substantially homogenous population of cells of any one phenotype, e.g., a cardiomyoctye, a striated muscle cell, a smooth muscle cell, a neuron, a hematopoietic cell or a cartilage cell.

A system is further provided by this disclosure. The system comprises, or alternatively consists essentially of, or yet further consists of, (a) a laser light source to produce an incident light, (b) a sensor configured to collect or detect second-harmonic light generated from the incident light, and (c) a plurality of cells comprising at least an undifferentiated stem cell and a differentiated cell comprising a noncentrosymmetric structure.

Figure 1:
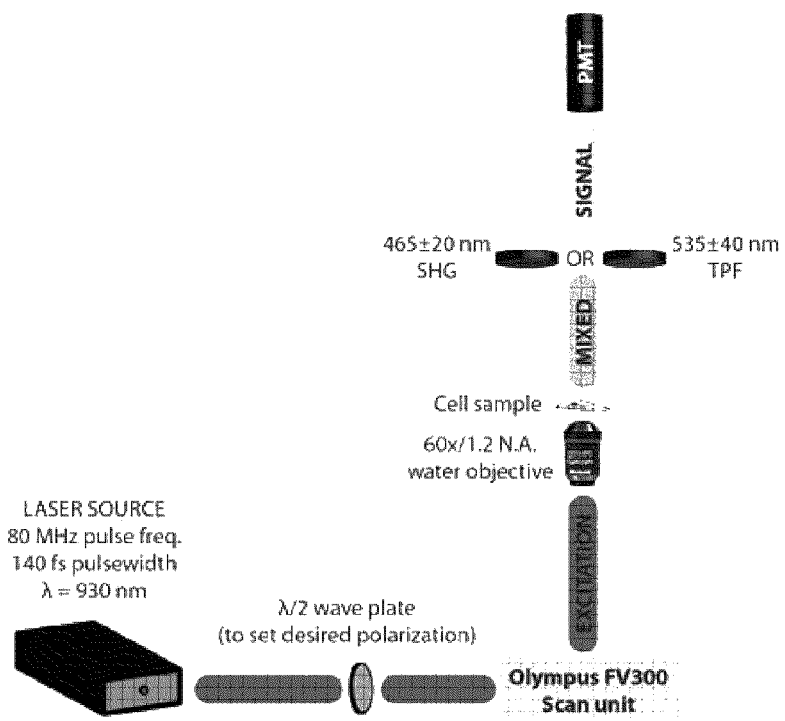
FIG. 1 illustrates a SHG/TPF microscope setup. A Ti:Sapphire laser tuned to 930 nm and producing 140 fs pulses at an 80 MHz repetition rate is used as the excitation source for both two photon fluorescence (TPF) and second harmonic generation (SHG). A half-wave plate modulates the polarization of the excitation beam. The beam is coupled into an Olympus FluoView 300 scan head and focused onto the sample with a 60×/1.2 numerical aperture (N.A.) objective. The signal (TPF or SHG) is separated from the excitation beam using narrow bandpass filters and collected by a photomultiplier tube (PMT). Both TPF and SHG are collected in the same beam path, but sequentially, in order to avoid image registration issues. Powers at the sample range from 30-50 mW.

Some or all of the figures are schematic representations for exemplification; hence, they do not necessarily depict the actual relative sizes or locations of the elements shown. The figures are presented for the purpose of illustrating one or more embodiments with the explicit understanding that they will not be used to limit the scope or the meaning of the claims that follow below.

DETAILED DESCRIPTION

Definitions

The practice of the present invention will employ, unless otherwise indicated, conventional techniques of tissue culture, immunology, molecular biology, microbiology, cell biology and recombinant DNA, which are within the skill of the art. See, e.g., Sambrook, Fritsch and Maniatis (1989) Molecular Cloning: A Laboratory Manual, 2$^{nd}$ edition; F. M. Ausubel, et al. eds. (1987) Current Protocols In Molecular Biology; the series Methods in Enzymology (Academic Press, Inc.): PCR 2: A Practical Approach (1995) (M. J. MacPherson, B. D. Hames and G. R. Taylor eds.); Harlow and Lane, eds. (1988) Antibodies, A Laboratory Manual; Harlow and Lane, eds. (1999) Using Antibodies, a Laboratory Manual; and R. I. Freshney, ed. (1987) Animal Cell Culture.

All numerical designations, e.g., pH, temperature, time, concentration, and molecular weight, including ranges, are approximations which are varied (+) or (−) by increments of 1.0 or 0.1, as appropriate. It is to be understood, although not always explicitly stated that all numerical designations are preceded by the term "about". It also is to be understood, although not always explicitly stated, that the reagents described herein are merely exemplary and that equivalents of such are known in the art.

As used in the specification and claims, the singular form "a," "an" and "the" include plural references unless the context clearly dictates otherwise.

As used herein, the term "comprising" is intended to mean that the compositions and methods include the recited elements, but do not exclude others. "Consisting essentially of" when used to define compositions and methods, shall mean excluding other elements of any essential significance to the combination when used for the intended purpose. Thus, a composition consisting essentially of the elements as defined herein would not exclude trace contaminants or inert carriers. "Consisting of" shall mean excluding more than trace elements of other ingredients and substantial method steps. Embodiments defined by each of these transition terms are within the scope of this invention.

The term "isolated" as used herein refers to molecules or biological or cellular materials being substantially free from other materials, e.g., greater than 70%, or 80%, or 85%, or 90%, or 95%, or 98%. In one aspect, the term "isolated" refers to nucleic acid, such as DNA or RNA, or protein or polypeptide, or cell or cellular organelle, or tissue or organ, separated from other DNAs or RNAs, or proteins or polypeptides, or cells or cellular organelles, or tissues or organs, respectively, that are present in the natural source and which allow the manipulation of the material to achieve results not achievable where present in its native or natural state, e.g., recombinant replication or manipulation by mutation. The term "isolated" also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides, e.g., with a purity greater than 70%, or 80%, or 85%, or 90%, or 95%, or 98%. The term "isolated" is also used herein to refer to cells or tissues that are isolated from other cells or tissues and is meant to encompass both cultured and engineered cells or tissues.

As used herein, "stem cell" defines a cell with the ability to divide for indefinite periods in culture and give rise to specialized cells. At this time and for convenience, stem cells are categorized as somatic (adult), embryonic or induced pluripotent stem cells. A somatic stem cell is an undifferentiated cell found in a differentiated tissue that can renew itself (clonal) and (with certain limitations) differentiate to yield all the specialized cell types of the tissue from which it originated. An embryonic stem cell is a primitive (undifferentiated) cell from the embryo that has the potential to become a wide variety of specialized cell types. Non-limiting examples of embryonic stem cells are the HES2 (also known as ES02) cell line available from ESI, Singapore and the H1 or H9 (also know as WA01) cell line available from WiCell, Madison, Wis. Pluripotent embryonic stem cells can be distinguished from other types of cells by the use of markers including, but not limited to, Oct-4, alkaline phosphatase, CD30, TDGF-1, GCTM-2, Genesis, Germ cell nuclear factor, SSEA1, SSEA3, and SSEA4. An -induced pluripotent stem cell (iPSC) is an artificially derived stem cell from a non-pluripotent cell, typically an adult somatic cell, produced by inducing expression of one or more stem cell specific genes.

The term "culturing" refers to the in vitro propagation of cells or organisms on or in media of various kinds. It is understood that the descendants of a cell grown in culture may not be completely identical (i.e., morphologically, genetically, or phenotypically) to the parent cell. By "expanded" is meant any proliferation or division of cells.

"Differentiation" describes the process whereby an unspecialized cell acquires the features of a specialized cell such as a heart, liver, or muscle cell. "Directed differentiation" refers to the manipulation of stem cell culture conditions to induce differentiation into a particular cell type. "Dedifferentiated" defines a cell that reverts to a less committed position within the lineage of a cell. As used herein, the term "differentiates or differentiated" defines a cell that takes on a more committed ("differentiated") position within the lineage of a cell. As used herein, "a cell that differentiates into a mesodermal (or ectodermal or endodermal) lineage" defines a cell that becomes committed to a specific mesodermal, ectodermal or endodermal lineage, respectively. Examples of cells that differentiate into a mesodermal lineage or give rise to specific mesodermal cells include, but are not limited to, cells that are adipogenic, leiomyogenic, chondrogenic, cardiogenic, dermatogenic, hematopoetic, hemangiogenic, myogenic, nephrogenic, urogenitogenic, osteogenic, pericardiogenic, or stromal.

As used herein, the term "differentiates or differentiated" defines a cell that takes on a more committed ("differentiated") position within the lineage of a cell. "Dedifferentiated" defines a cell that reverts to a less committed position within the lineage of a cell.

As used herein, a "pluripotent cell" defines a less differentiated cell that can give rise to at least two distinct (genotypically and/or phenotypically) further differentiated progeny cells. In another aspect, a "pluripotent cell" includes a Induced Pluripotent Stem Cell (iPSC) which is an artificially derived stem cell from a non-pluripotent cell, typically an adult somatic cell, produced by inducing expression of one or more stem cell specific genes. Such stem cell specific genes include, but are not limited to, the family of octamer transcription factors, i.e., Oct-3/4; the family of Sox genes, i.e., Sox1, Sox2, Sox3, Sox 15 and Sox 18; the family of Klf genes, i.e., Klf1, Klf2, Klf4 and Klf5; the family of Myc genes, i.e., c-myc and L-myc; the family of Nanog genes, i.e., OCT4, NANOG and REX1; or LIN28. Examples of iPSCs are described in Takahashi et al. (2007) Cell advance online publication 20 Nov. 2007; Takahashi & Yamanaka (2006) Cell 126:663-76; Okita et al. (2007) Nature 448:260-262; Yu et al. (2007) Science advance online publication 20 Nov. 2007; and Nakagawa et al. (2007) Nat. Biotechnol. Advance online publication 30 Nov. 2007.

A "multi-lineage stem cell" or "multipotent stem cell" refers to a stem cell that reproduces itself and at least two further differentiated progeny cells from distinct developmental lineages. The lineages can be from the same germ layer (i.e., mesoderm, ectoderm or endoderm), or from different germ layers. An example of two progeny cells with distinct developmental lineages from differentiation of a multilineage stem cell is a myogenic cell and an adipogenic cell (both are of mesodermal origin, yet give rise to different tissues). Another example is a neurogenic cell (of ectodermal origin) and adipogenic cell (of mesodermal origin).

A "composition" is also intended to encompass a combination of active agent and another carrier, e.g., compound or composition, inert (for example, a detectable agent or label) or active, such as an adjuvant, diluent, binder, stabilizer, buffers, salts, lipophilic solvents, preservative, adjuvant or the like. Carriers also include biocompatible scaffolds, pharmaceutical excipients and additives proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. Carbohydrate excipients are also intended within the scope of this invention, examples of which include but are not limited to monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and myoinositol.

"Substantially homogeneous" describes a population of cells in which more than about 50%, or alternatively more than about 60%, or alternatively more than 70% or alternatively more than 75%, or alternatively more than 80%, or alternatively more than 85%, or alternatively more than 90%, or alternatively, more than 95%, of the cells are of the same or similar phenotype. Phenotype can be determined by a pre-selected cell surface marker or other marker.

A population of cells intends a collection of more than one cell that is identical (clonal) or non-identical in phenotype and/or genotype.

The term treating (or treatment of) a neurodegenerative disorder or condition refers to ameliorating the effects of, or delaying, halting or reversing the progress of, or delaying or preventing the onset of, a neurodegenerative condition as defined herein.

A mammalian stem cell, as used herein, intends a stem cell having an origin from a mammal. Non-limiting examples include, e.g., a murine, a canine, an equine, a simian and a human.

An immature stem cell, as compared to a mature stem cell, intends a phenotype wherein the cell expresses or fails to express one or more markers of a mature phenotype. Examples of such are known in the art, e.g., telomerase length or the expression of actin for mature cardiomyoctyes derived or differentiated from a less mature phenotype such as an embryonic stem cell.

EXEMPLARY EMBODIMENTS

This disclosure provides experimental data to demonstrate a new method for identifying live suspension and plated pluripotent stem cells (PSCs)-derived cardiomyocytes (CMs) at different stages of maturity. Such a method is free of fluorescent labeling and genetic modification. The method is based on second harmonic generation (SHG), a nonlinear optical technique in which a laser beam incident on a 'harmonophore' is coherently scattered into a signal that is twice the frequency of the excitation beam.

Data presented here demonstrates the high specificity of the SHG signal to the PSC-CM phenotype, which is attributed to the bundled domains only being present in the PSC-CMs following the directed differentiation of PSCs to the cardiac lineage. PSC-CMs at a differentiation time as early as day 7.5 could be identified based on this signal and the dependence of the SHG signal intensity on the maturity of the myofilament network was demonstrated.

Human stem cell-derived cardiomyocytes are immature relative to mature cadiomyocytes isolated from a subject. Both the lengthened duration of human embryonic development and the imperfect nature of in vitro directed differentiation protocols for stem cells contribute to this immaturity. This disclosure shows for the first time that CMs as immature as those differentiated from stem cells in as few as 7.5 days, before the observation of spontaneous contractions, have the ability to generate SHG signals. The timing coincides roughly with the earliest expression of fluorescent proteins that are driven by the MHC (day 5) and human myosin light chain 2v (day 7) promoters in transgenic hESC-CMs. SHG can be elicited from a single myofilament, so this timing is expected. The ability of SHG to detect PSC-CMs at differentiation day 7.5 is comparable to that of methods using reporter cell lines and much higher than the mitochondrial staining method.

The present data shows that 90-100% of plated CMs defined by α-actinin staining and 90% of MHC-positive day 24 suspension cells were identified by SHG. In comparison, the number of cardiomyocytes isolated by the mitochondrial staining method was 60-90% of the number defined by α-actinin staining and the purification experiments were demonstrated using more mature embryoid bodies (days 50 and 90).

SHG can also be used to discriminate PSC-CMs with different degrees of maturity of the myofilament network, at least up to 30 days after contraction begins. Furthermore, the generation of SHG signals in CMs derived from both hESCs and iPSCs suggest the technique can be universally applied for the identification of CMs derived from any stem cell source.

In general, the present disclosure shows that SHG is able to identify cells differentiated from stem cells, so long as the differentiated cells can generate second-harmonic light from incident light, since stem cells are unable to generate second-harmonic light from the incident light. Such differentiated cells include those possessing a noncentrosymmetric structure.

Non-limiting examples of noncentrosymmetric structure include myosin, collagen, microtubule, axon and dendrite. Accordingly, cardiomyocytes, skeleton muscle cells, smooth muscle cells and neurons can all be identified by SHG, even if they are differentiated from stem cells in vitro or ex vivo.

Once the cells are identified, then the present disclosure also provides methods for separating them from other cells, including from cells that also are differentiated, having noncentrosymmetric structure but is at a slightly different differentiation stage.

The present data also shows that it is important to suspend the differentiated cells with collagenase and not trypsin so that individual cells retain enough of a structured intracellular myofilament network to allow SHG to occur.

These results have established SHG as a potential label-free, non-genetic technique for identifying PSC-CMs from undifferentiated PSCs with a sensitivity superior to current PSC-CM purification techniques. The ability to detect the early myofilament development in the PSC-CMs makes this a potentially sensitive technique to detect CMs at early differentiation time points even prior to contraction and discriminate between cells at different levels of maturity (sarcomeric development). The SHG signals are sufficiently intense enough to enable sorting speeds comparable to current flow cytometer speeds (thousands of cells/sec) and the ability to detect signals in suspension cells prepared in collagenase that do not degrade the myofilament network.

In one embodiment, therefore, the present disclosure provides a method for isolation of a stem-cell derived differentiated cell. The method entails illuminating an incident light onto a plurality of stem-cell derived cells that comprise at least an undifferentiated cell and a differentiated cell possessing a noncentrosymmetric structure, wherein the differentiated cell generates second-harmonic light from the incident light; and isolating the differentiated cell identified by the second-harmonic light.

The term "centrosymmetric" refers to a point group which contains an inversion center as one of its symmetry elements. In such a point group, for every point (x, y, z) in the unit cell there is an indistinguishable point (-x, -y, -z). Point groups lacking an inversion center (non-centrosymmetric) are further divided into polar and chiral types. A chiral point group is one without any rotoinversion symmetry elements. Rotoinversion (also called an 'inversion axis') is rotation followed by inversion; for example, a mirror reflection corresponds to a twofold rotoinversion.

Certain cellular structures and organized proteins are known to contain noncentrosymmetric structures, such as myosin, collagen, microtubule, axon and dendrite. Accordingly, mature cells that contain such cellular structures or proteins can generate second-harmonic light. Examples of such cells, without limitation, include cardiomyocytes, skeleton muscle cells, smooth muscle cells and neurons.

Further, as discovered, unexpectedly, in the present disclosure, even cardiomyocytes, skeleton muscle cells, smooth muscle cells or neurons that are differentiated from stem cells can contains such structures. In one aspect, a noncentrosymmetric structure is present at as early as 7 days following initiation of different ion (?) from a stem cell. Accordingly, the methods of above embodiments are applicable to even immature cardiomyocyte, an immature skeleton muscle cell, an immature smooth muscle cell or an immature neuron.

As used herein, "immature" refers to a cell differentiated from a stem cell in an artificial environment, and are necessarily different from differentiated cells that are isolated from an animal subject. In some aspects, "immature" refers to a cell that is differentiated, in vitro, from a stem cell wherein the duration of the differentiation is less than about 180 days, or alternatively less than 150 days, 120 days, 90 days, 60 days, or 30 days.

In one aspect, the differentiated cell is an immature cardiomyocyte.

As provided, stem cells include any cells that are capable to differention to a more mature cell type. Non-limiting examples of stem cells include an embryonic stem cell, an induced pluripotent stem cell, a multipotent stem cell, an oligopotent stem cell, or a unipotent stem cell.

Types of incident lights suitable for generating second-harmonic light are known in the art. In one aspect, the incident light has a wavelength from about 700 nm to about 1500 nm. In another aspect, the incident light has a wavelength of at least about 700 nm, or 750 nm, 800 nm, 850 nm, 900 nm, 950 nm, or 1000 nm. In another aspect, the incident light has a wavelength of no more than 1500 nm, or 1400 nm, 1300 nm, 1200 nm, 1100 nm, 1050 nm, 1000 nm, 950 nm or 900 nm.

In one aspect, the incident light comprises pulses having a width of wave from about 70 fs to about 10 ps. In another aspect, the width is at least about 80 fs, 90 fs, 100 fs, 110 fs, 120 fs, 130 fs, 140 fs, 150 fs, 200 fs, 500 fs, 1 ps, 2 ps, 3 ps, 4 ps or 5 ps. In another aspect, the width is no more than about 140 fs, 150 fs, 160 fs, 170 fs, 180 fs, 190 fs, 200 fs, 250 fs, 500 fs, 1 ps, 2 ps, 3 ps, 4 ps, 5 ps or 10 ps.

In one aspect, the incident light has a repetition rate from about 1 KHz to about 100 MHz. In one aspect, the repetition rate is at least about 1 KHz, 2 KHz, 3 KHz, 5 KHz, 10 KHz, 20 KHz, 30 KHz, 40 KHz, 50 KHz, 80 KHz, 100 KHz, 500 KHz, 1 MHz, 2 MHz, 3 MHz, 4 MHz, 5 MHz, 10 MHz, 20 MHz, 30 MHz, 40 MHz, 50 MHz, 60 MHz, 70 MHz, or 80 MHz. In another aspect, the repetition rate is no more than about 100 MHz, 90 MHz, 80 MHz, 70 MHz, 60 MHz, 50 MHz, 40 MHz, 30 MHz, 20 MHz, 10 MHz, or 1 MHz.

The methods of the present disclosure do not require the use of an exogenous detectable label to be added to the cell to assist identification. Also not required is genetic engineering to introduce identifiable features to the cells. Therefore, in one embodiment, the differentiated cell being identified does not comprise a fluorescent or radioactive label.

In some embodiment, it is provided that, prior to illuminating the incident light onto the cells, the method further entails suspending the cells in a medium. Another unexpected finding of the present disclosure that trypsin, as compared to other enzymes such as collagenase, is not suitable for such suspension. Therefore, in one embodiment, when performing such suspension, collagenase, rather than trypsin, is used.

Another embodiment of the present disclosure provides a method of isolating cells comprising passing a plurality of cells through a device comprising (a) a laser light source to cast an incident light on the cells and (b) a sensor configured to collect or detect second-harmonic light generated from the incident light, wherein the cells comprise at least an undifferentiated stem cell and a differentiated cell comprising a noncentrosymmetric structure; identifying the differentiated cell by the second-harmonic light generated on the cell; and collecting the differentiated cell.

In one aspect, the sensor is one or more lenses configured to collect second-harmonic light generated from the cell. The lenses can be, but are not necessarily, organized into a microscope. In another aspect, the sensor includes a receiver of second-harmonic light that characterizes the light. In this aspect, lenses are not required.

In some aspects, the incident light is illuminated to the cells in a lightsheet illumination geometry. Such a geometry creates a thin (e.g., from about 0.5 µm to about 5 µm, or alternatively from about 1 to about 4 µm) sheet of light with substantially uniform. In one aspect, the incident light is created as a Bessel beam. The term "Bessel beam" as used here, refers to an electromagnetic field whose amplitude is described by a Bessel function. In one aspect, the Bessel beam propagates with no diffraction or substantially no diffraction within a longitudinal distance of at least about 50 µms.

Also provided, in one embodiment of the present disclosure, is a population of differentiated cells isolated from the method of any of the above embodiments. The population of cells can be substantially homogeneous in terms of phenotype or differentiation stage.

Further provided is a method of distinguishing two cells of different differentiation stages, comprising: culturing one or more stem cells under conditions to allow the stem cells to differentiate to two differentiated cells at different differentiation stages, at least one of which comprises a noncentrosymmetric structure; illuminating an incident light on the differentiated cells; and distinguishing the two differentiated cells by examining second-harmonic light generated on at least one of the two differentiated cells.

In some aspects, the two differentiated cells have undergone differentiation with the same procedure, but the durations of the differentiation are different. In one aspect, the difference of duration is at least 1 day, or alternatively at least 2 days, 3 days, 4 days, 5 days, 6 days, 7 days, 8 days, 9 days, 10 days, 15 days, 20 days, 25 days, or 30 days.

In some aspects, the two differentiated cells have undergone different differentiation procedure such that the method can be used to determine the impact of the procedures on differentiation.

Once the methods are provided, systems for carrying out the methods are also provided. In one embodiment, provided is a system comprising (a) a laser light source to produce an incident light, (b) an sensor configured to collect or detect second-harmonic light generated from the incident light, and (c) a plurality of cells comprising at least an undifferentiated stem cell and a differentiated cell comprising a noncentrosymmetric structure. Characteristics and examples of light sources, sensors, and cells are provided above.

EXAMPLE

Example 1. Identification of Stem Cell-Derived Cardiomyocytes

Methods and Materials
Maintenance and Differentiation of Pluripotent Stem Cells

Human embryonic stem cells (ES Cell International, HES-2) were cultured following a feeder-independent culture procedure that utilized mTeSR 1 (Stem Cell Technologies) and Matrigel (BD Biosciences). The cell lines were differentiated to the cardiac lineage following Yang et al. *Nature* 453:524 (2008). In a 5% $CO_2$/5% $O_2$/90% $N_2$ environment, the embryonic stem cell lines were treated with the following: 0.5 ng $ml^{-1}$ BMP4 in mTeSR 1 complete media for days 0-1; 10 ng $ml^{-1}$ BMP4, 5 ng $ml^{-1}$ bFGF, and 3 ng $ml^{-1}$ activin A in StemPro-34 medium (Invitrogen) (medium 1); 150 ng $ml^{-1}$ DKK1 and 10 ng $ml^{-1}$ VEGF in StemPro-34 medium for days 4-8 (medium 2); medium 2 plus 5 ng $ml^{-1}$ bFGF from day 8 until the end of the differentiation process. On day 12, the cells were transferred to a 5% $CO_2$/air/37° C. incubator and maintained with DMEM containing 15% FBS, 2 mM L-Glutamine and 1×NEAA (sustenance media). All growth factors were purchased from R&D systems.

Vector-free human induced pluripotent stem cells (hiPSCs) (purchased from WiCell, iPS—DF19-9-7T) were maintained as described above. For cardiac differentiation, a matrix-overlay directed differentiation procedure was developed. The growth factor exposure timeline from Yang et al. *Nature* 453:524 (2008) was combined with monolayer culture and matrigel overlay, motivated by Zhang et al. *Circulation* 122, A20724 (2010). In brief, hiPSCs were passaged 1:2 and allowed to grow to confluency on Matrigel-coated 78.5 $cm^2$ culture plates. The cells were suspended using Accutase and plated on 3.8 $cm^2$ plates as a monolayer, on growth factor reduced (GFR) Matrigel (BD Biosciences) and in complete mTeSR 1, for 1 day. Day 0: the cell monolayer was overlaid with 1:4 GFR Matrigel; after 45 min at 37° C. for gelation, medium 1 (from the hESC differentiation protocol, above) was added atop the gel and the cells were incubated in 5% $CO_2$/5% $O_2$/90% $N_2$/37° C. environment. Day 3: medium 1 was replaced by medium 2. Day 4: the cells were transferred to a 5% $CO_2$/air/37° C. incubator. Day 6: medium 2 was replaced with sustenance media, with which the cells were maintained thereafter. Spontaneously contracting monolayers were observed on day 8.

Preparation of PSC-CMs for SHG Analysis

PSC-CMs were prepared in suspension using either trypsin or collagenase. For trypsin, 0.05% trypsin-EDTA (Invitrogen) was used for 8 minutes, trypsininhibited, and washed. For collagenase, cells were treated with type II collagenase (200 U/ml; Invitrogen) for 1 hour while micropipetting every 15 minutes. After 1 hour, the uniformly suspended cells were pelleted and washed. Suspension cells were fixed by treatment with 4% paraformaldehyde for 15 min at room temperature. In separate experiments, PSC-CMs were also re-plated on gelatincoated glass coverslips and allowed to mature in sustenance media for different time periods ranging from 4 hours to 10 days. Cells were then fixed by treatment with 4% paraformaldehyde for 15 min at room temperature. PSC-CMs were immunostained for a-actinin (Sigma) or myosin heavy chain (MHC; Gene Tex) with Alexa Fluor 488 (AF488) goat antimouse $IgG_1$ (Invitrogen) to confirm the CM phenotype. Stem cells were stained for Oct3/4 (Santa Cruz Biotechnology) with AF488 goat anti-mouse $IgG_{2b}$ to confirm pluripotency of the undifferentiated cells.

Laser Scanning Confocal Microscope

A femtosecond pulsed Ti:sapphire laser (Coherent Chameleon Ultra) tuned to $\lambda=930$ nm was used as the excitation source for SHG and two-photon fluorescence (TPF) microscopy (FIG. 1). The laser (140 fs pulses, 80 MHz repetition rate) was coupled into a laser scanning confocal microscope (Olympus FluoView FV300/IX81) equipped with a 60×/1.2 NA water immersion objective. Power at the sample ranged from 40-60 mW, corresponding to single-pulse energies of 500-750 pJ. The forward propagating SHG and two-photon fluorescence (TPF) signals were collected by the condenser lens, isolated by 465/20 and 535/40 bandpass filters, respectively, and delivered to a photomultiplier tube. Image analysis was performed using the FV300 software and imaging analysis software (Fiji/ImageJAv1.44). For second harmonic imaging of individual sarcomeres, a line scan was performed along individual sarcomeres.

Image Acquisition and Analysis

Images were acquired using the FV300 software at scan speeds of 9.1 µs per pixel. The zoom and the number of pixels generated per scan (e.g., 1024×1024 vs. 2048×2048) were varied according to the size of the cell imaged. To account for the resulting variation in dwell time per micron, all image intensities were linearly scaled to an identical dwell time per area before comparison. For 3D imaging, stack scans were performed over ranges of 10-20 µm, depending on cell thickness, with a step size of 1 µm. To obtain total cell SHG and TPF intensity values, the boundary of each cell was manually selected, and the signal intensity above background noise was measured and summed across all stacks.

Results

SHG Signals in PSC-CMs are Specific to the Sarcomere A-Bands

Figure 2:
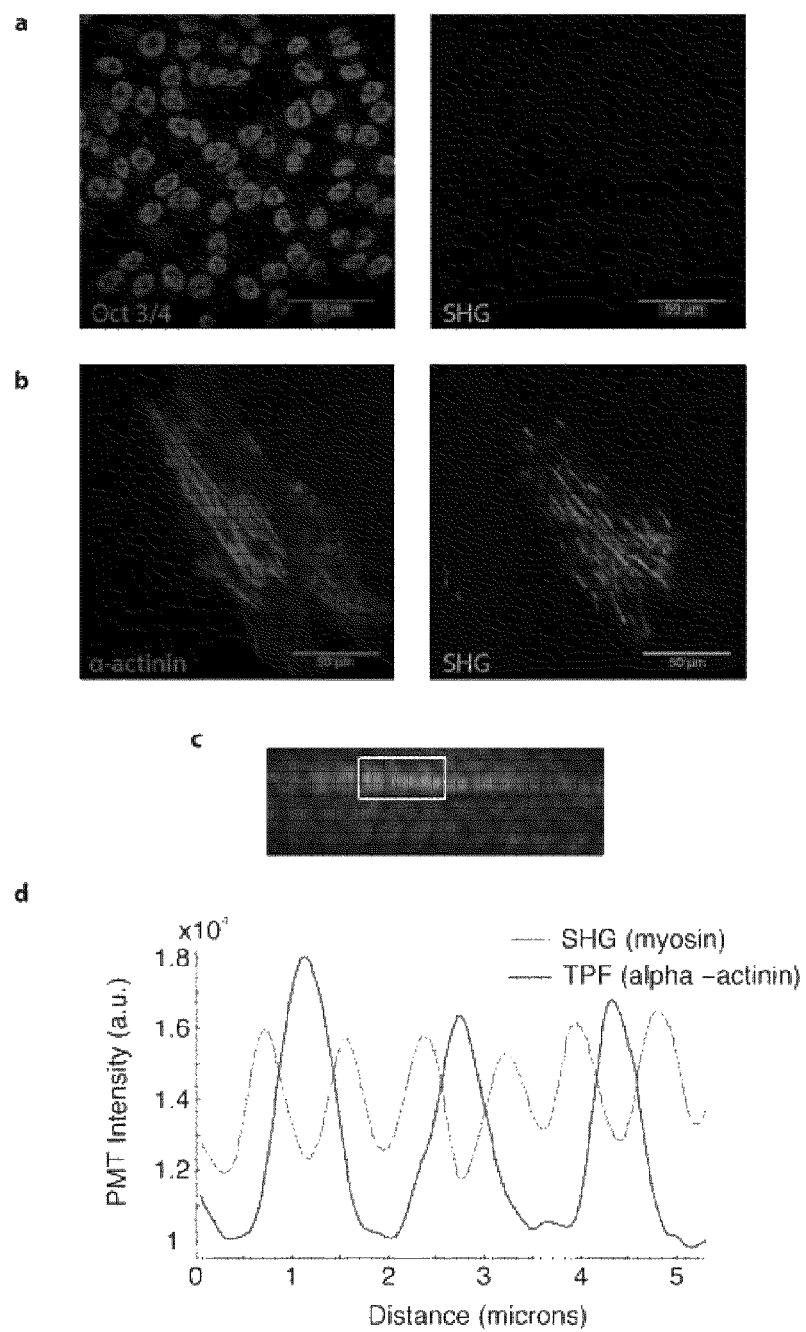
FIG. 2a-d shows that SHG is specific to sarcomeric A-bands in PSC-CMs. (a) TPF of HES2 cells immunostained for the pluripotency marker Oct-3/4 (red, shown as dark gray, anti-Oct-3/4-AF488) and the corresponding SHG (green, shown as light gray) image of the same cells. No SHG is visible. (b) TPF (red, shown as dark gray, anti-α-actinin-AF488) in a day 10 replated HES2-derived cardiomyocyte, with corresponding SHG (green, shown as light gray). (c) A zoomed image of two myofilaments with SHG (green, shown as light gray) and anti-α-actinin-AF488 TPF (red, shown as dark gray) overlaid, showing the localization of SHG to either side of the sarcomere Z-bodies. Below (d) is the horizontal intensity profile of the boxed portion of the myofilament in (c).

Stem cells positively stained for Oct 3/4 showed no appreciable SHG signal (FIG. 2a) while immature PSC-CMs generated an SHG signal that was specific to that phenotype. FIG. 2b shows SHG and TPF images taken sequentially of a day 30 PSC-CM replated on gelatin and allowed to mature for 10 days prior to fixation and immunostaining for α-actinin.

These images were overlaid to localize the SHG source relative to α-actinin. FIG. 2c is a magnified section of the overlay image showing SHG signals emanating from either side of the α-actinin stained Z-bodies, which is consistent with previous studies involving non-human embryonic cardiomyocytes. The intensity plot in FIG. 2d reveals that the SHG signal appears as two distinct bands between each Z-disc, with the bands separated by 0.765±0.033 µm. The Z-disc separation was 1.597±0.022 µm. The pattern is consistent with the myosin containing A-band being the source of the signal, and the dark gap between the SHG bands being the H-zone.

SHG Signal Intensity Distinguishes Time-Dependent Reestablishment of Myofilaments in PSC-CMs SHG and TPF signal intensities from the total cell volume were obtained from PSC-CMs re-plated for 4 hours, 2 days, 4 days, and 10 days (FIG. 3a). A clear trend of increasing signal strength for both SHG and TPF with reestablishment of myofilaments and increasing cell maturity following re-plating was observed. A one-way analysis-of-variance (ANOVA) test was performed to determine if the cell populations were distinguishable from one another by their total-cell SHG intensities alone. The null hypothesis was rejected with a p-value of $3.44\times10^{-18}$ and a Tukey post-hoc test further demonstrated the distinguishability of the means of all of the cell groups from one another with $p<0.05$ (FIG. 3b). The results indicate that the total SHG signal of a cell can be used to quantify the content of sarcomeric myosin in the cell and hence, the maturity of a CM's myofilament network.

The change in the SHG:TPF ratio (log-intensity) as the cells matured was also quantified (FIG. 3c). This ratio starts relatively high at the 4 hour time point but drops substantially by day 2 and then in-creases from day 4 to day 10. The observations are best interpreted in the context of analogous electron microscopy (EM) studies. In EM studies, the hours immediately following trypsinization and replating were characterized by CM rounding and a loss of myofilament structural integrity. The myofilaments formed loose aggregates at the center of the cells, visible as disorganized, filamentous contrast upon EM, and lacked the dense Z-bodies seen in well-formed CMs. Degradation of myofilament structure would randomize harmonophore orientation and reduce SHG intensity, while the loss of Z-bodies would reduce anti-a-actinin-AF488 TPF.

The ratio of the two would remain relatively high in the initial hours, as observed. Following the initial phase of plating, the cells spread out and EM studies indicate that the Z-bodies are rebuilt before the myofilaments begin to sarcomerize. The development of Z-bodies prior to sarcomerization is reflected by the drop in the SHG:TPF ratio observed at day 2. In the following days, myofilaments are synthesized and sarcomerize, the SHG capacity of individual CMs increases and the SHG:TPF ratio grows. The proportion of α-actinin positive cells that generate SHG signals followed a similar pattern (FIG. 3d).

Collagenase-but Not Trypsin-Digested Suspension PSC-CMs Maintain SHG Signal

Trypsin is a critical enzyme in most protocols for digesting cardiac tissue, but it has long been appreciated that trypsinization of CMs results in the immediate disorganization and partial degradation of intracellular myofilaments. After observing that the intensity of the SHG signal is strongly dependent on the remodeling of the myofilament network, the applicants sought to optimize SHG signals that could be detected in PSC-CMs prepared in suspension using different protocols. SHG signals could not be detected in any suspension PSC-CMs prepared with trypsin, confirming that trypsin induces myofilament degradation, which consequently affects the SHG signal. However, collagenase dissociated PSC-CMs (differentiation day 24) held in suspension for at least 2 hours maintained a strong capacity for SHG. 90% of MHC positive PSC-CMs (n=20) generated SHG signals. FIG. 4a shows an example of an SHG image of a suspension PSC-CM (day 24) prepared with collagenase. The spatial distribution of the SHG signal in these cells was strongly indicative of well-maintained myofilament networks even after 2 hours in suspension.

The MHC-immunostained day 24 PSC-CMs from above were imaged at low magnification in order to determine the specificity of the SHG signal for identifying PSC-CMs. For each field of view, three images were taken using light scattering microscopy (FIG. 4c), TPF microscopy (anti-MHC-AF488, FIG. 4d) and SHG microscopy (FIG. 4e). In total, 1 out of 35 non-MHC+ cells generated a SHG signal, corresponding to a specificity of 97.1% (34/35).

SHG Can be Used to Distinguish Suspension PSC-CMs of Varying Maturity

Total cell SHG intensity was obtained from PSC-CMs differentiated for 20 and 40 days, prepared as single suspension cells using collagenase, and fixed with paraformaldeyhde. SHG signals could be generated in both samples, though on average, day 40 cells generated 3.5 times the number of SHG photons per cell when compared to the day 20 cells (FIG. 4b, p=0.023, n=15 and 16 for day 20 and 40, respectively).

Thus, the dependence of total cell SHG on the maturity of a CM myofilament network was sensitive enough to allow the resolution of groups of suspension PSC-CMs at different differentiation time points. SHG signals could be detected from suspension PSC-CMs as early as differentiation day 7.5, prior to the observation of spontaneous contractions.

Day 7.5 PSC-CMs, suspended with collagenase, plated for 1 hour, and immunostained for MHC showed an average 10-fold reduced SHG intensity compared to day 20 cells (FIG. 4b, right).

Several methods are currently available to purify PSC-CMs from a heterogeneous population of cells, but they are limited in scope and/or performance. The techniques that allow the earliest isolation of viable cardiac lineage cells involve genetic modification and can neither be ubiquitously applied nor used clinically. Noninvasive techniques such as Percoll gradient centrifugation and mitochondrial labeling rely on CMs to be matured for months so that the sorting may be reasonably specific. However, many cardiac cells of interest have immature metabolic phenotypes, including CMs with substantial proliferative capacity and CMs of certain disease environments (i.e., cardiac hypertrophy).

In contrast to these techniques, this example has shown that SHG can potentially be a label-free and nongenetic method to accurately identify PSC-CMs. Human stem cell-derived cardiomyocytes are extremely immature relative to mature cells. Both the lengthened duration of human embryonic development and the imperfect nature of in vitro directed differentiation protocols for stem cells contribute to this immaturity. This example shows for the first time that CMs as immature as those differentiated from stem cells in as few as 7.5 days, before the observation of spontaneous contractions, have the ability to generate SHG signals. Though this example did not test earlier time points, the timing coincides roughly with the earliest expression of fluorescent proteins that are driven by the MHC (day 5) and human myosin light chain 2v (day 7) promoters in transgenic hESC-CMs. SHG can be elicited from a single myofilament, so this timing is expected. The ability of SHG to detect PSC-CMs at differentiation day 7.5 is comparable to that of methods using reporter cell lines and much higher than the mitochondrial staining method.

The data shows that 90-100% of plated CMs defined by α-actinin staining and 90% of MHC-positive day 24 suspension cells were identified by SHG. In comparison, the number of cardiomyocytes isolated by the mitochondrial staining method was 60-90% of the number defined by α-actinin staining and the purification experiments were demonstrated using more mature embryoid bodies (days 50 and 90). SHG can also be used to discriminate PSC-CMs with different degrees of maturity of the myofilament network, at least up to 30 days after contraction begins. Furthermore, the generation of SHG signals in CMs derived from both hESCs and iPSCs suggest the technique can be universally applied for the identification of CMs derived from any stem cell source.

Vibrational spectroscopy has been investigated as a tool for non-invasively identifying and analyzing stem cell-derived cardiomyocytes. While vibrational spectroscopy is a promising technique for cellular analysis on many fronts, SHG, as a second order nonlinear process, occurs with much higher conversion efficiencies than vibrational spectroscopic processes. Consequently, an SHG-based cell sorter may allow the label-free identification of PSC-CMs at speeds that are orders of magnitude faster than sorters based on Raman or infrared spectroscopy. Additionally, the specificity of SHG to a single intracellular source in PSC-CMs makes collected signals readily interpretable and adaptable for stem cell biologists.

These results support the feasibility of integrating SHG within a flow cytometric scheme for the rapid and automated analysis and sorting of PSC-CMs. Such a scheme would require the detection of SHG signals from PSC-CMs that have been digested into single suspension cells (FIG. 4a) and delivered into the microfluidic channel of a cytometer. This example also shows that it is important to suspend the PSC-CMs with collagenase and not trypsin so that individual PSC-CMs retain enough of a structured intracellular myofilament network to allow SHG to occur.

These results have established SHG as a potential label-free, non-genetic technique for identifying PSC-CMs from undifferentiated PSCs with a sensitivity superior to current PSC-CM purification techniques. The ability to detect the early myofilament development in the PSC-CMs makes this a potentially sensitive technique to detect CMs at early differentiation time points even prior to contraction and discriminate between cells at different levels of maturity (sarcomeric development). The SHG signals are sufficiently intense enough to enable sorting speeds comparable to current flow cytometer speeds (thousands of cells/sec) and the ability to detect signals in suspension cells prepared in collagenase that do not degrade the myofilament network.

Example 2. Setup of a Second Harmonic Generation Microscopy System

Figure 5:
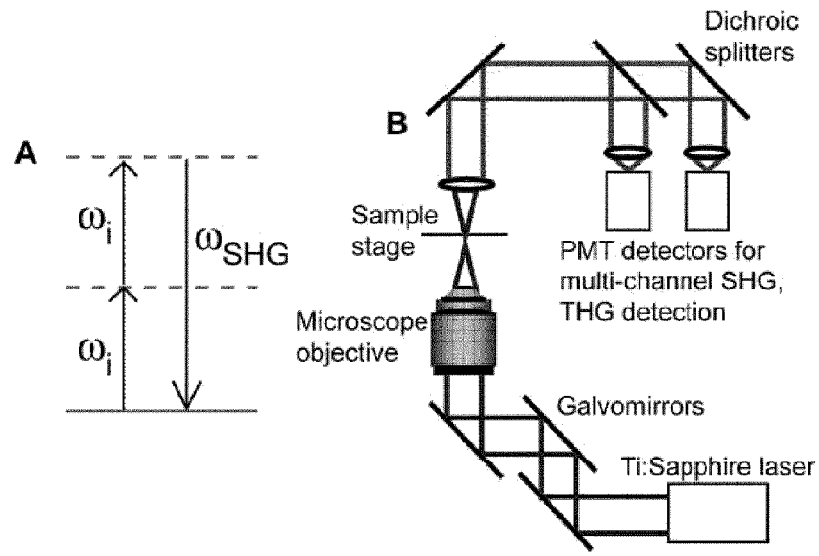
FIG. 5A is an energy diagram depicting the second harmonic generation (SHG) process in which two incident laser photons at frequency $\omega_i$ are converted to a photon at twice the frequency $\omega_{SHG}=2\omega_i$ (or half the wavelength) when interacting with materials with noncentrosymmetric properties. Dashed lines indicate virtual states.
FIG. 5B is schematic of a laser scanning confocal microscope equipped with a Ti:Sapphire femtosecond laser that is used for SHG microscopy. The system is, in principle, equivalent to a fluorescence confocal microscope but is equipped with a laser, optical filters, and detectors specific for SHG detection. Detection of harmonic signals is performed in the forward direction, although both forward and backward detection can be implemented in our setup.

Second harmonic generation (SHG) microscopy is a nonlinear optical technique used to image the structural properties and dynamic processes of live cells in both in vitro and in vivo environments. SHG involves the nonlinear interaction of photons and materials that possess a noncentrosymmetric molecular arrangement, resulting in the conversion of the incident light from a frequency ω, to a second harmonic at 2ω, (FIG. 5A). A laser scanning confocal microscope using a femtosecond (~100 fs) pulsed laser source (800 nm, 20-40 mW, 80 MHz) for excitation used for SHG cell imaging is shown in FIG. 5B.

Because the 2ω, signal comes intrinsically from the sample, SHG does not require the addition of exogenous labels, making it ideally suited for noninvasive live cell imaging. Any potential issues of perturbing the biological state of the cell by the introduction of external dyes can be avoided. Because SHG is a parametric process that does not involve photon absorption (as in fluorescence), there is no photobleaching of the SHG signal, which allows for continuous and long term dynamic cell monitoring. For skeletal and cardiac muscle cells, the second harmonic signal has proven to be an ideal image contrast mechanism for visualizing the sarcomere, the fundamental unit of these muscle cells.

The anisotropic band (A-band) region of the sarcomere, consisting of myosin filaments arranged in a semicrystalline order, is an efficient SH signal generator while the isotropic band (I-band) region made up of actin filaments, generates no SH signal. The result is a repeated pattern of bright and dark striped regions in an SHG image that allows the sarcomere structure to be visualized with an accuracy as low as 20 nm. Also noteworthy is that the M band, the region at the center of the A-band, normally has a diminished SH signal due to destructive interference from oppositely oriented myosin molecules but when the cell is stretched, these molecules are separated which leads to constructive interference and the generation of SH signals.

An advantage of SHG microscopy is the ability for real-time monitoring of the contraction of cells with high temporal resolution and for long periods of times, due to the strong and nonphotobleaching nature of the SHG signal, without inducing cell photodamage. Rapid imaging of the spacing between the sarcomeres as a function of time as the cell contracts and stretches allows information of the dynamic functional properties of these cells to be obtained. While imaging large (~20×20 μm) region is one option of monitoring cell contractility, the frame rate is typically too slow to resolve fast contractile dynamics. An alternative scheme to capture dynamic sarcomere contractions at millisecond time frames is to perform a laser line-scan at several hundred to thousand Hz perpendicularly across a row of sarcomeres.

This example explores the use of SHG microscopy to study the intrinsic structure and contractile dynamics of hESC-CMs as they are stimulated and induced to maturation. The sensitive response of the SH signal to the structure and orientation of the sarcomere structure and the ability to monitor dynamic cellular contractions in real-time makes SHG an ideal optical technique to study hESC-CM maturation. No other technique, to the inventor's knowledge, offers the same simple, noninvasive, and accurate means to obtain quantitative dynamic contractile rates of live CM cells. This parameter can then be directly correlated to information of the MHC isoforms that are present, which allows functional and molecular cellular information to be linked together. Furthermore, the contractile rate can potentially be used in the future as a parameter for the clinical assessment of the degree of maturity of hESC-CMs for the purposes of isolating these cells.

Example 3. Characterization of Second-Harmonic Features of PSC-CMs

The methods of the present disclosure directly addresses the need for new technology that can separate and isolate differentiated cell lineages from undifferentiated stem cells and other undesired cell types, which is currently a major challenge in regenerative medicine and a bottleneck in the development of novel stem cell therapies.

This example provides a method for sorting high purity live PSC-CM populations without needing to label or genetically modify the cells. It is based on second harmonic generation (SHG), a label-free nonlinear optical technique that can directly detect the presence of myosin rod domains, which should only be found in myocytes and absent in undifferentiated PSCs and other cell types, based on the unique optical property of organized myosin bundles to function as intrinsic 'harmonophores', converting light of wavelength λ (from an intense ultrashort laser pulse) to light of wavelength (λ/2) due to their non-centrosymmetric ordered structure. By using this λ/2 second harmonic (SH) signal as the parameter for sorting cells, the SHG approach is expected to be very accurate for identifying PSC-CMs since it can directly detect the thick filaments of the sarcomere or myosin bundles, an ideal and more definitive indicator of the contractile CM phenotype. It is also contemplated that it can identify CMs at specific differentiation time points and at an earlier differentiation time than the mitochondrial dye method, which requires a significant increase in mitochondria in order to present the PSC-CMs as a distinct population from other cell types. By integrating SHG spectroscopy with microfluidic devices, this example develops an SHG-based optofluidic cell sorter platform. In addition to its potential clinical use, the SHG optofluidic sorter is expected to have a broad impact on other applications that utilize PSC-CMs, such as cardiac drug development and testing, tissue engineering, or basic research studying PSC-CM hypertrophy and development.

Since there are currently no established and accepted methods for purifying PSC-CM populations, this method would be a major advancement and innovation in cell separation technologies for this specific biological application. To the inventors' knowledge, this method would introduce the first and only approach for obtaining high purity live PSC-CM populations without needing any genetic modification or labeling of the cells, which is a novel and important aspect of this technology that will allow the intended use of these cells for clinical transplantation, in-vitro cardiac drug testing, and other applications.

As an example, consider the case where live PSC-CMs are needed for transplantation. Although it remains unclear exactly how many PSC-CMs will be needed in myocardial cell replacement therapy, assuming $1\times10^7$ to $1\times10^8$ PSC-CMs for the purposes of this example. With an anticipated analytical throughput of several thousand cells/sec for the SHG cell sorter (which is comparable to the sorting speeds at which commercial fluorescence based flow sorters are operated in practice for accurate sorting) and an estimated 50% yield of CMs in the directed differentiation of PSCs, it would take anywhere from 3 to 24 hours to obtain the desired number of cells. This time increases significantly to over 200 hours (8 days) if $1\times10^9$ CMs are needed. Given the long time needed to obtain such large populations, it will likely not be feasible to sort fresh viable PSC-CMs hours immediately prior to patient transplantation. In practice, however, sorting of these cells immediately preceding their use is not necessarily required since it is typically known in advance the patients that are on a waiting list needing treatment (e.g., donor organs or cell replacement therapy).

Therefore, one can envision a scenario in which cells are continuously sorted by a SHG flow sorter in advance to build up a large population of PSC-CMs over time. These cells can be cryopreseved for long-term storage until they are needed while still maintaining their viability and functionality. Cryopreserved cultured fetal CMs have been successfully transplanted into subcutaneous and myocardial scar tissue, which formed spontaneously and regular beating myocardium-like tissue. Cryopreservation of hESC-CMs using Rhoassociated kinase (ROCK) inhibitor has also been successfully demonstrated.

It is contemplated that these SHG cell sorters will be implemented into Good Manufacturing Practice (GMP) stem cell facilities to ensure the manufacturing of quality products for clinical applications.

A. Studying the SHG Properties of PSC-CMs as a Function of their Differentiation and Maturation The presence of myosin rod domains and sarcomeres in early developing PSC-CMs, as confirmed by immunostaining and transmission electron microscopy (TEM) data, suggests that these cells have the requisite harmonophores needed to generate SH signals. This study can test the hypothesis that PSC-CMs and their maturity can be accurately identified by the SH signal. The results can provide a systematic evaluation of the SHG properties of PSC-CMs as they differentiate and mature over time. Several key questions can be addressed in this study. Can PSC-CMs generate a detectable SH signal and how accurate is it for identifying PSC-CMs? How does the SH signal intensity vary as a function of PSC-CM maturation, and does it have the resolving power to identify cells at different days post-differentiation (i.e., cell maturation)? What is the earliest time point that differentiating CMs can be detected by SHG?

This study can also demonstrate that PSC-CMs prepared as individual suspension cells retain their ability to generate SH signals. This is important for two reasons. First, the SHG flow cytometer will only work with suspension cells. Second, it is generally believed that cardiac myocytes that are kept in suspension cultures over a long period may not be able to maintain their mature myofibrillar apparatus, which would result in degradation of the SH signals. The protocol that the inventors have established for preparing CMs in suspension minimizes perturbation of their sarcomere architecture. This can be used for generating PSC-CM suspension cells and experiments can be conducted to determine the SH properties and the extent of the SH signal degradation, if any, due to any myofibrillar disassociation that may occur. SHG characterization of PSC-CMs can be performed using a standard laser scanning confocal microscope optimized for SHG microcopy using a tight laser focusing condition to ensure that optimal SHG data from these samples are collected. The first experiments are performed on PSC-CMs plated on substrates to ensure cells have optimal development of contractile architecture. These are followed by equivalent experiments performed on suspension PSC-CMs. PSC-CMs at different time points post-differentiation, prepared for these measurements. The accuracy of the SH signal to identify the CM phenotype and the degree of maturation can be independently verified by immunostaining SHG-positive cells for α-actinin or α-tropomyosin, two known CM markers, and correlating the fluorescence and SHG data. Although this example is directed to the derivation of CMs from an induced pluripotent stem cell (iPSC) line, the SHG technique is generally applicable for the identification of CMs derived from other stem cell sources (e.g., embryonic).

Methods

Derivation of Cardiomyocytes (CMs) from Induced Pluripotent Stem Cells (iPSCs)

The inventors have derived CMs from induced pluripotent stem cells (iPSCs) (WiCell iPS OF 19-9-7T) using established cardiac differentiation protocols and isolated at different time points post-differentiation (day 8-12, 1 day increments, day 9-40, 5 day increments). Briefly, iPSCs were detached as small clusters using accutase (Stem Cell Technologies) and transferred to low-attachment plates to allow embryoid body (EB) formation. The EBs were cultured in suspension and hypoxia for 12 days in Stem Pro-34 medium (Invitrogen) with 2 mM L-glutamine (Invitrogen), 0.4 mM monothioglyerol (Sigma) and 50 µg/ml ascorbic acid (Sigma) with addition of 10 ng/ml BMP4 (R&D Systems), 3 ng/ml activin A (R&D Systems) and 5 ng/ml bFGF (Invitrogen) from day 1-4, 10 ng/ml VEGF (R&D Systems) and 150 ng/ml DKK1 (R&D Systems) from day 4-8, followed by 10 ng/ml VEGF, 150 ng/ml DKK1 and 5 ng/ml bFGF from day 8-12. The directed differentiation protocol yields, on average, more than 50% of spontaneously beating cardiospheres.

CMs are prepared as both plated cells on glass bottom (No. 1 thickness) culture dishes (MatTek Corp.) and in suspension for SHG analysis. For plated samples, cells are plated for a short time period (4 to 10 hours) prior to analysis. For suspension samples, cells are left in suspension for different time periods (0 to 5 hours) prior to analysis.

Preparing Single Cell PSC-CM Suspensions

Figure 9:
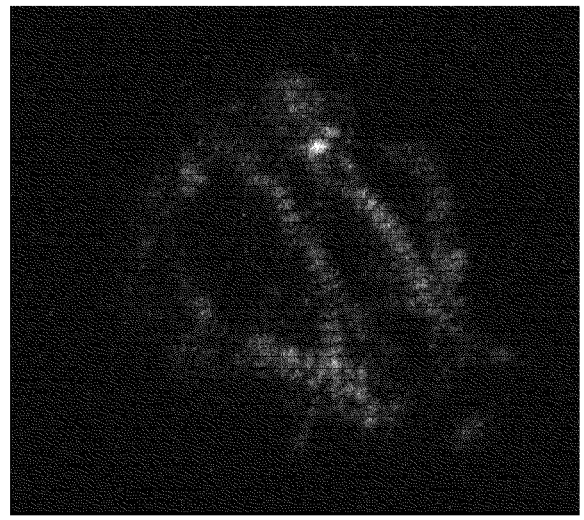
FIG. 9 shows a SHG image of a suspension PSCCM showing that PSC-CMs in suspension for several hours still generate a strong SH signal and retain their sarcomere architecture. This result is critical, because it shows that suspension PSC-CMs can be detected in a flow environment.

For single CMs, spontaneously contracting cardiospheres are digested into single cells with collagenase II (200 U/mL) at 37° C. for 30 min with constant stirring. Collagenase are used in lieu of trypsin because during separate experiments involving the isolation of neonatal murine CMs, it was observed that over 60% of the cells were able to retain their rod shape physiological morphology and myofilament assembly. This is in stark contrast to trypsinized cells, which resulted in almost 100% of the cells being rounded up and collapsed, indicative of disassembly of the contractile architecture. PSC-CMs isolated using this collagenase protocol also showed the ability to retain their sarcomere structures and SH signal generating ability (see below and FIG. 9).

SH and Fluorescence Correlation Study of Stem Cell Derived Cardiomyocytes

A confocal laser scanning fluorescence microscope (Olympus Fluoview 300) redesigned to add SHG capability to the system can be used. An ultrashort (100 fs) pulsed Ti:Sapphire laser (Coherent Chameleon) operating at 930 nm and 80 MHz is used as the excitation source to generate SH signals at 465 nm in PSC-CMs, which is detected by a PMT detector with a 465 nm narrow bandpass filter. A 525 nm bandpass filter can also be used for fluorescence (Alexa 488) imaging via two-photon excitation. The confocality of the system enables three-dimensional sectioning of a cell and the entire volume of a cell to be imaged. PSC-CMs (~30 day post-differentiation) can be isolated and prepared as single plated cells on gridded coverslip glass bottom culture dishes. Fixed cells are fluorescently stained with CM-specific markers (a-actinin, tropomyosin, myosin heavy chain) and a nuclear dye to identify the PSC-CMs from the undifferentiated PSCs and non-CM cell types. SHG imaging analysis is performed on these cells. For each cell, three-dimensional fluorescence and SHG images of the cell volume are obtained by performing z-stack confocal imaging over a ~20 µm distance (~0.5 µm step size). Using image analysis software (ImageJ, Matlab), the fluorescence and SH signals integrated over the entire volume is quantified and correlated to determine the sensitivity and specificity of the SH signal to accurately discriminate PSC-CMs from PSCs and other non-CM cells. Pure populations of undifferentiated iPSCs are used as a negative control. A second set of equivalent experiments are performed on PSC-CMs left in suspension for different time periods after digestion of the beating clusters into singe cells (0-5 hours), which are then fixed, fluorescently stained, and analyzed.

Figure 6:
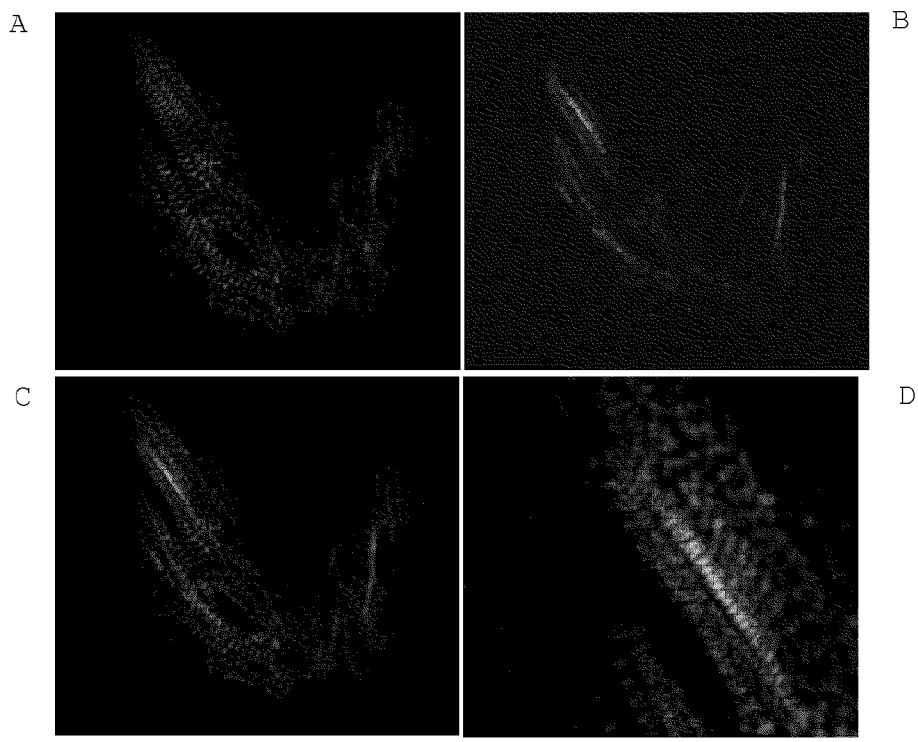
FIG. 6A-D are microscopic images. (A) Two photon fluorescence and (B) SHG false color images of an α-actinin stained (Alexa 488) PSC-CM. (C) Overlay image confirming SH signals originate from the sarcomere structures. (D) Close up image of a section of the cell showing the sarcomere striation pattern. The myosin based source of the SH signal is confirmed based on the offset positions of the SH and fluorescence signals.
Figure 7:
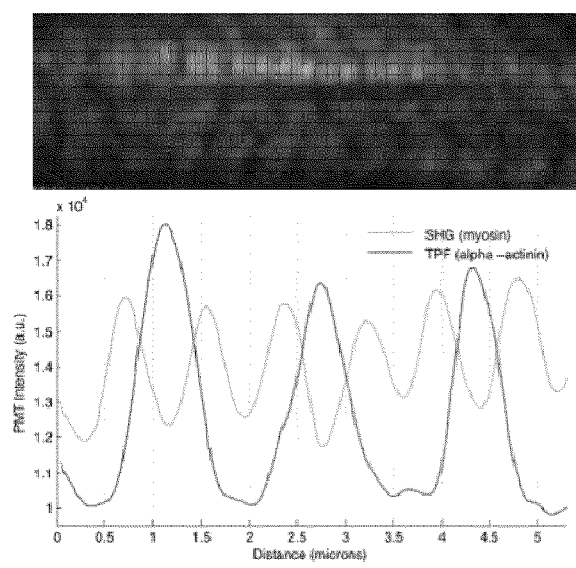
FIG. 7 shows a fluorescence and SHG overlay image of a sarcomere row in a PSC-CM (upper panel) and SHG and fluorescence intensity plot show quantification of SHG intensity, sarcomere spacing, and periodic/offset pattern of the two signals (bottom panel).

FIG. 6 shows that PSC-CMs do, in fact, generate SH signals. PSC-CMs (day 30 differentiation, 6 days post plating) were fluorescently stained for α-actinin with Alexa 488 to confirm CM phenotype and origin of the SH signal. Using a 60×, 1.4 NA water immersion objective, ~30 mW laser power, and imaging speeds as fast as 15 [!s/pixel, two photon fluorescence and SHG images were obtained from the same sample. False color two photon fluorescence (FIG. 6A), SHG (FIG. 6B), and overlay (FIG. 6C) images of the PSC-CM show that these cells generate a detectable SH signal and that the signal originates from the sarcomeric structure in the cell. A close up image and intensity plot (FIG. 6D and FIG. 7) of a section of the cell shows that the SH and fluorescence signals are not colocalized but, instead, are spatially offset slightly. This shows that the source of the SH signal is myosin and not α-actinin based. Undifferentiated stem cells (negative control) exhibited no SH signals (data not shown).

SH Analysis of PSC-CMs at Different Maturation Stages and Early Differentiation Time Points Equivalent experiments are performed on PSC-CMs isolated at time points 9-30 days post-differentiation in ~5 day increments. In addition to performing the SHG-fluorescence correlation study described above, the SHG signal intensities integrated over the entire cell volume will also be quantified and plotted as a function of differentiation time point to determine the ability to discriminate cells at different maturation stages based on their SH signal intensity. Cells at differentiation time points >30 days are also analyzed until no change in SH signal intensity as a function of differentiation time is observed. Moreover, the earliest differentiation time point at which these cells can generate detectable SH signals is determined by isolating PSC-CMs at day 8-12 post-differentiation for SHG analysis.

Figure 3:
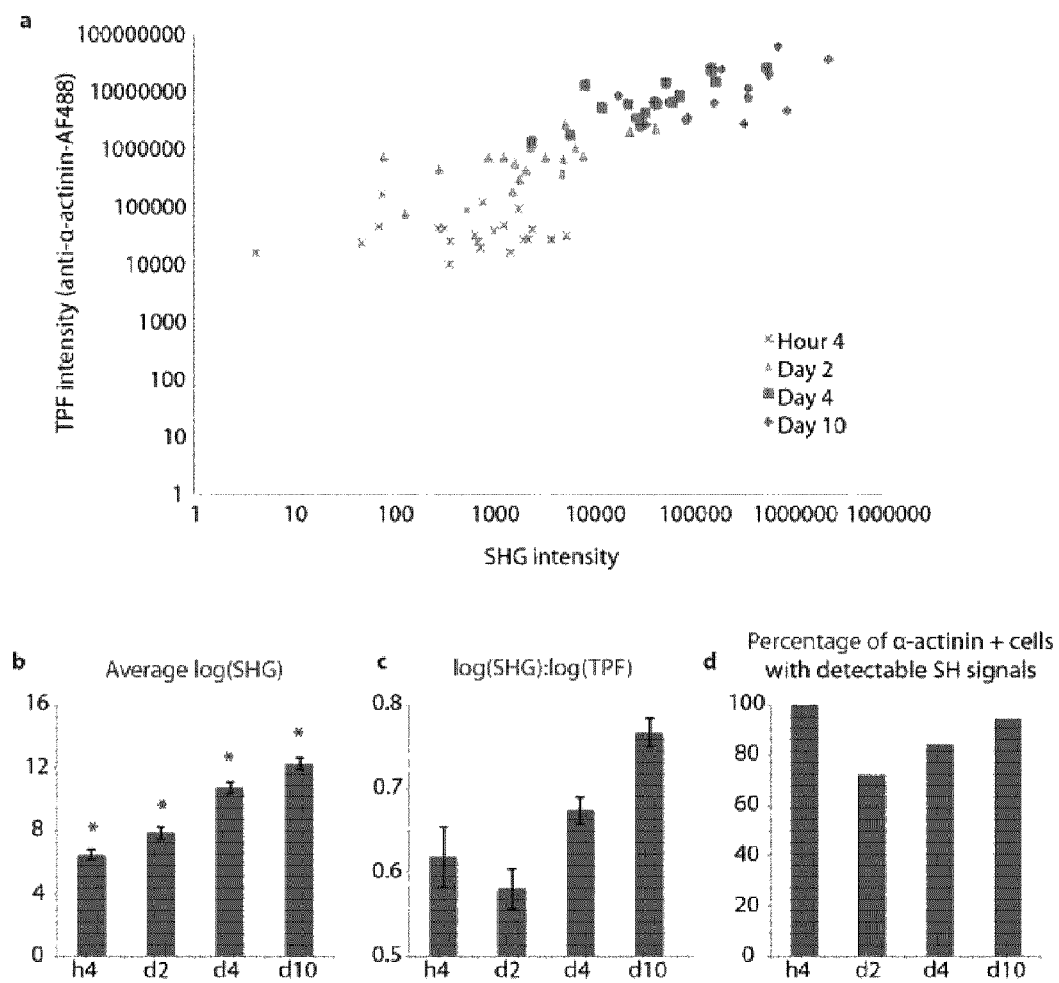
FIG. 3a-d shows that total-cell SHG signal intensity increases with myofilament network maturity in re-plated PSC-CMs. HES2-derived cardiospheres were dissociated into single cells and re-plated on gelatin for 4 hours, 2 days, 4 days and 10 days. Following maturation, the cells were fixed, immunostained for α-actinin, and imaged. (a) Comparison of the anti-α-actinin-AF488 TPF intensity to SHG intensity for each cell sampled. Only SHG positive cells are plotted. (b) Mean and standard error for log(SHG) values from the data plotted in FIG. 3a. A one-way analysis-of-variance (ANOVA) demonstrated that the populations are very likely distinct ($p=3.44\times10^{-18}$), and a Tukey post-hoc test showed that all log-means were significantly different from one another with $p<0.05$ (*). Only SHG positive cells were considered. (c) Mean and standard error of the SHG:TPF ratio at the time points examined. See text for a biological explanation. (d) The percentage of α-actinin-positive cells at each time point producing a detectable SHG signal.

This range is chosen because beating of the clusters is usually first observed around this time. The preliminary results indicate that SHG can discriminate PSC-CMs at different stages of contractile development. SHG analysis was performed on PSC-CMs (30 day post-differentiation) that were plated for different lengths of time. FIG. 3 shows a plot of the total SH and α-actinin fluorescence intensity of the plated PSC-CMs. This data highlights several important points. One, the SH signal intensity (x-axis) can discriminate PSC-CMs that were plated for different times (0.2, 1, 4 and 10 days), suggesting that the SH signal has the potential to detect the degree of sarcomere reorganization and development.

Second, almost all (>95%) of the 4 hr and 10 day cells that were probed are SHG positive, whereas ~65% of the 1 and 4 day cells are SHG positive. This suggests that after the beating cluster is digested into individual cells, the 4 hr plated cells still retain their sarcomere structures, which begin to break down during its reorganization at 1-4 days, followed by reorganization of the sarcomere assembly at 10 days post-plating.

Although these studies did not probe PSC-CMs at different post-differentiation time points, the results provide supporting evidence that SHG can detect sarcomere reorganization and development; therefore, without being bound by theory, it is anticipated that the SH signal intensity should be able to detect the maturation of the PSC-CM contractile architecture and discriminate between PSC-CMs at different postdifferentiation times (8 to 30 days).

Figure 4:
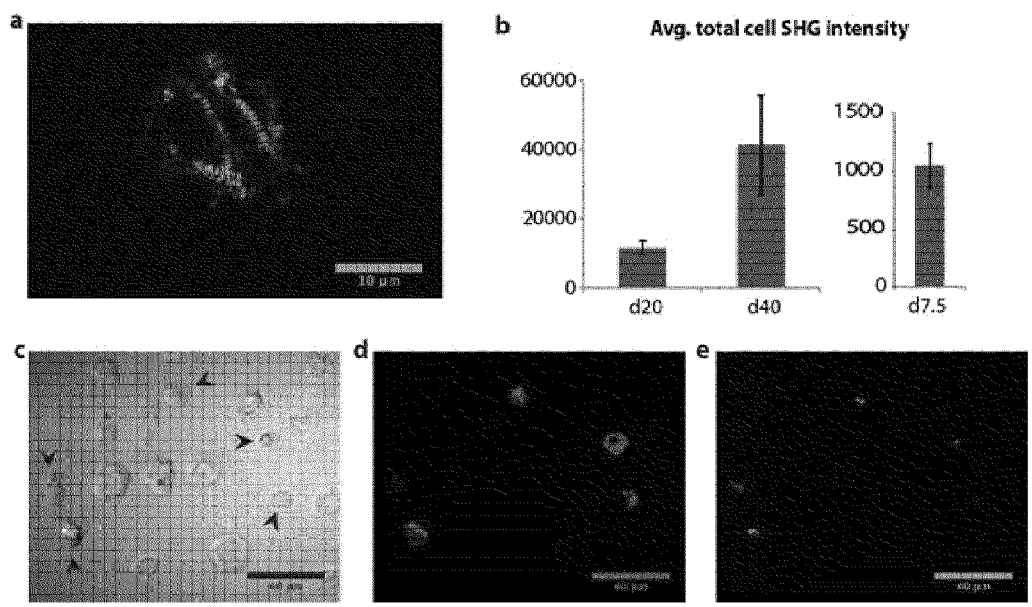
FIG. 4a-e show that hiPSC-CMs digested with collagenase type II produce differentiation day-dependent SHG signals. (a) Day 24 hiPSC-derived cardiomyocytes in monolayers were dissociated into single cells using collagenase type II, retained in suspension for 2 hours, fixed and imaged for SHG. Myofilaments and capacity for SHG were retained in these cells, in contrast to trypsinized hiPSC-CMs (not shown). (b) hiPSC-CMs were dissociated as described, fixed at days 20 and 40 of differentiation and probed for SHG. Day 40 cells displayed significantly stronger total-cell SHG than day 20 cells (p=0.023, n=16 for d20, n=15 for d40). Day 7.5 PSC-CMs from a separate differentiation batch were similarly analyzed and found to have a 10-fold reduced total-cell SHG than day 20 cells (n=10, right column, plotted separately to magnify scale). Day 24 hiPSC-CMs were imaged using (c) light scattering microscopy to identify all cells in a given field-of-view (arrows indicate MHC positive cells), (d) TPF microscopy (anti-MHC-AF488) to identify CMs, and (e) SHG microscopy. Results were correlated to estimate the specificity of SHG signal to identify PSC-CMs (specificity=97.1%).

PSC-CMs Left in Suspension Retain their Sarcomere Architecture for Several Hours Individual PSC-CMs (20 day post-differentiation) were prepared by using the collagenase digestion protocol and leaving the cells in suspension for over 2 hours before they were fixed and stained (α-actinin) to confirm their CM phenotype. Individual suspension cells were immobilized by sandwiching them between two coverslips in solution. The SH image in FIG. 4 shows that these cells are still capable of generating strong SH signals, with the striation patterns still clearly discernable. In fact, 100% of all α-actinin positive cells that were probed (10 out of 10) generated similar SH signals/images. These results confirm that suspension PSC-CMs can be prepared with their contractile architecture still intact for several hours, which would be within the time frame needed to analyze and sort the cells with the SH flow cytometer.

Endothelial and fibroblast cells may potentially generate SH signals due to the presence of e.g., microtubules, a known SHG-active structure. However, SHG has typically been observed in dense, ordered microtubule arrays, such as in neurons, suggesting that any SHG signals observed in individual endothelial or fibroblast cells would be much weaker and that these cells can be eliminated on the basis of the SHG intensity. The data here showed only SHG signals from PSC-CMs and not from other cells in the population. PSCs cultured in feeder-free conditions will eliminate the presence of feeder fibroblasts, and the addition of BMP4 and activin A in stage 1 of the cardiac differentiation protocol will inhibit the ectodermal lineage or neural differentiation. In addition to cardiac cells, skeletal and smooth muscle cells also have myosin bundles. Therefore, the ability to distinguish PSC-CMs from these cells is a potential problem. However, it is known that skeletal myogenesis is nearly non-existent in both spontaneous differentiation of PSC-CMs and in directed cardiogenesis. Smooth muscle cells (SMCs) have about half the myosin found in striated muscles and lacks similar sarcomere organization. Since the actin-to-myosin ratio for these non-striated muscle cells is 15:1 compared to 7:1 in striated CMs, it is expected that any SH signals generated in SMCs will likely be much weaker, thus allowing their discrimination from CMs based on signal strength. A SMC antibody (smooth muscle actin or myosin heavy chain) can be used to identify SMCs for SHG characterization. Collagen is a well-known SHG-active species, but collagen can be removed from the sample after digestion of the beating cluster into single cells.

Although the ability to identify contractile PSC-CMs (atrial and ventricular) for cell replacement therapy is expected, the SHG technique will likely not be able to identify subsets of CMs (pacemaker, Purkinje, atrial, ventricular). This drawback does not preclude the possibility of using this method to isolate contractile PSC-CMs for subsequent conditioning into the desired cell subtype. For example, immature atrial CMs at a stage prior to their terminal differentiation stage can be converted into ventricular CMs when exposed to a ventricular environment.

Figure 8:
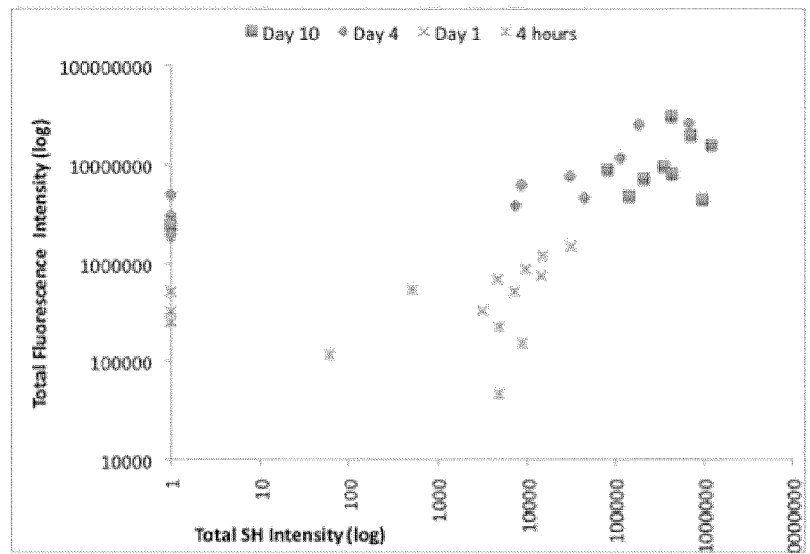
FIG. 8 shows fluorescence and SHG total intensity of PSC-CMs plated for different lengths of time. Results indicate that SH intensity can be used to discriminate PSC-CMs at different stages of contractile architecture development.

The process of plating the cells may induce significant reorganization of the sarcomere structure (i.e., FIG. 8), which would introduce an experimental artifact that may adversely affect the ability to discriminate PSC-CMs at different differentiation time points based on differences in SHG signal intensity. If so, the SHG maturation experiments can be performed directly on suspension PSC-CMs, which have been shown to generate SH signals. Fluorescence immunostaining of α-actinin and tropomyosin are proposed as two markers to confirm CM phenotype and maturation stage. Additional markers include without limitation Islet 1 or Nkx2.5, in combination with the aforementioned markers, to further delineate more immature cells. The use of fluorescence stains should not adversely affect SHG characterization of the PSC-CMs, as shown herein and also in literature (Plotnikov, et al. Biophysical Journal, Vol. 90:693-703 (2006)), as long as the dye emission does not overlap with the SH signal (465 nm).

B. Studying the Effectiveness of a Bessel Beam Lightsheet Excitation Geometry for Generating SH Signals from PSC-CMs The tight laser focusing condition is the most standard excitation scheme that is used in SHG microscopy for generating SH signals from individual cells. This trusted optical scheme can be used as above to perform the initial SHG characterization studies of PSC-CMs, a biological system that has not, until now, been characterized. In another embodiment, the cell can be flowing in solution down a microchannel in a random orientation relative to the laser beam. Because the sarcomeres are fairly randomly distributed in the cell (diameter ~10 µm), insufficient spatial overlap of the sarcomere structures with the tightly focused laser spot (diameter ~1 µm) may occur, which would prevent SH signals from being reliably and reproducibly generated from the cells. In one aspect, the laser beam can probe a greater fraction of the cell consistently, and therefore most of the sarcomeres in the cell if desired. For example, a scanned Bessel beam excitation scheme, which creates a light sheet illumination pattern, can be used to enable a larger fraction of the cell to be uniformly probed as it flows through the excitation beam. Secondly, another important consideration is the orientation of the sarcomere structures with respect to the laser polarization, since it is known that there is a preferential alignment between them that generates the strongest SH signal. This can be an issue with the proposed SH cell sorter, since the random orientation of the flowing cell in the sorter will prohibit any control over this alignment. A circularly polarized excitation beam that has been shown to be able to generate SH signals in semi-regular biological structures can be used to address the sarcomere-polarization alignment issue.

Equivalent experiments of Experiment A can be carried out to test these embodiments for generating SH signals for discriminating PSC-CM cells.

Methods

Lightsheet Illumination Using a Scanned Bessel Beam

In order to effectively probe SH signals from a PSC-CM in flow, the optical excitation scheme should be able to rapidly and uniformly probe a large fraction of the PSC-CM in order to interrogate the full sarcomeric content of the cell within the time frame that the PSC-CM is within the excitation region.

Figure 10:
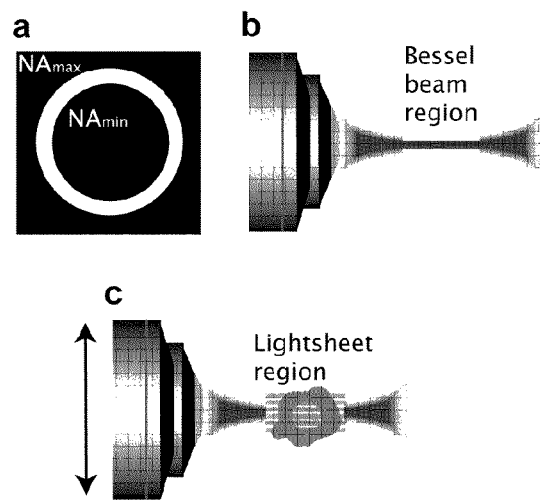
FIG. 10a shows an annulus mask that converts a laser beam to a Bessel beam.
FIG. 10b shows a Bessel beam with uniform axial intensity spanning tens of microns.
FIG. 10c Scanning of the laser along one direction (arrow) generates a lightsheet. Lightsheet probes a large fraction of the cell as it flows through the lightsheet (cell will flow perpendicular to the lightsheet, in a direction out of the plane of the paper).

Simply using a lower NA objective to yield a more defocused laser spot is not ideal because of the huge drop in power intensity, which will degrade the intensity dependent SH signal. Accordingly, in one aspect a lightsheet illumination geometry is used. This geometry creates a thin sheet of light with uniform and high intensities in 2-D that can reach several tens of microns along each axis. The cell passing perpendicularly through this light sheet will be relatively uniformly illuminated, allowing the entire sarcomeric content of the cell to be probed. To create the intense lightsheet pattern, a system for widefield isotropic multiphoton fluorescence imaging of single cells is used and applied towards whole cell detection of SH spectroscopic signals. This embodiment is based on Bessel beams, an electromagnetic field whose amplitude is described by a Bessel function. A true Bessel beam does not diffract as it propagates; however, in practice, approximate Bessel beams can be created that propagate with little to no diffraction over a limited longitudinal distance (50-60 µms). The Bessel beam is created by projecting the laser beam through a custom fabricated transmissive annulus mask (FIG. 10a) etched into an opaque aluminum coating on a quartz substrate. Masks with differing outer and inner diameters (NAmax, NAmin ranging from 0.1 to 0.6) will define a different Bessel beam with a specified central peak width and longitudinal extent. The beam through the mask is then imaged onto the back focal plane of the excitation objective (e.g., 10×, 0.3 NA), which generates a Bessel beam region at the objective focus (FIG. 10b). A light sheet is generated by rapidly scanning the laser beam along one axis with a spatial light modulator (SLM), galvanomirror, or resonant scanner (FIG. 10c). With scan rates faster than the dwell time of the flowing cell (tens of milliseconds) in the beam region, and the fact that SH signals have been generated from PSC-CMs in as little as 15 µs (see data above), SH signals should be detectable from the entire PSC-CM cell. Collection of the SH signals can be achieved by using the excitation objective in a backward propagating detection geometry, or alternatively using a separate counter-propagating objective with a higher numerical aperture (40×, 0.8 NA) for higher collection efficiencies.

SHG Excitation Using Circular Polarization

Using collagen rich tissue, the use of circularly polarized excitation light can be advantageous for SH analysis of biological samples. It eliminates the dependence of the SH signal on the orientation of the laser polarization relative to the SH generating biological structure. This allows for the detection of uniform SH signals from biological samples with semi-regular oriented structures.

In one aspect, this polarization scheme is implemented to probe suspension PSC-CMs, which intrinsically have randomly oriented sarcomeres, that can be randomly oriented as it flows in solution through the excitation region. A quarter wave plate can be used to convert the laser polarization from linear to circularly polarized before it is converted into the lightsheet geometry.

Samples

The same PSC-CM samples as described in Experiment A are prepared for this experiment. PSC-CM samples are prepared as individual suspension cells, which best mimics the conditions the cells used when delivered through the SH cell sorter. For analysis, the suspension cells are immobilized onto poly-l-lysine coated coverslips or sandwiched between substrates (flowing cells will be analyzed in Experiment C).

The prior demonstration of the lightsheet and polarization techniques for multiphoton and SHG applications suggests that these methods should be applicable in this study for addressing key issues in the development of a PSC-CM cell sorter. Another option available for generating a Bessel beam is the use of an achromat and axicon doublet to create an annular laser excitation pattern. In one aspect, galvanometers, SLMs, and resonant scanners can be used to enable scan rates in the kHz regime, which would correspond to a flow rate of ~1000 cells/sec. This can compensate for the rate at which the Bessel beam can be scanned to create the lightsheet relative to the rate at which the cell would flow through the lightsheet in the SHG sorter. As the cell flow rate is increased, there will come a point where the scan rate of the Bessel beam will not be fast enough to enable the lightsheet to probe the entire cell volume prior to the cell flowing out of the probe region. Galvanometers, SLMs, and resonant scanners can enable scan rates in the kHz regime, which would correspond to a flow rate of ~1000 cells/sec. These numbers are comparable to an estimated throughput of the SHG sorter based on the SHG signal acquisition times previously demonstrated, which can be as short as 15 µs. To achieve higher throughputs, an alternative design is available that creates a lightsheet using a cylindrical lens, which converts the Gaussian shaped beam into a thin lightsheet of over ~50×150 µm, thus eliminating the need for any scanning.

This scheme has been previously demonstrated for Raman imaging applications. There is, however, a tradeoff with this design. The lightsheet will not be as tightly focused compared to that created by the Bessel beams, which may adversely affect the SH signal intensity given its dependence on the laser intensity. An increase in the laser power can be used to compensate for this intensity drop.

C. Developing a Prototype SHG-Activated Flow Cytometer to Demonstrate Label-Free Sorting of PSC-CMs While Experiment A provided evidence that SH signals can be used to identify PSC-CMs, the measurements were not compatible with a flow sorting scheme. This section shows how to integrate the optical systems developed in Experiment B with microfluidic devices for SH analysis and sorting of PSC-CMs flowing through microchannels. The maximum analytical throughput (cells/sec) and sorting efficiency and accuracy can be quantified, and the viability of the sorted cells is assessed. The direct integration of the optical systems into a commercial fluorescence activated cell sorter (FACS), although appealing, has some limitations.

Microfluidic devices can be integrated with the above noted optical schemes from Experiment B. Microfluidic devices provide greater design control and flexibility. Parameters such as the physical dimensions of the microfluidic and optical components and flow rates can be more easily controlled. Multichannel microfluidic devices with optical based sorting as described above (below?) for other label-free cell sorting applications, can be used.

Although these systems will not be capable of reaching the analytical and sorting throughputs of FACS systems (10,000+ cell/sec), microfluidic systems will allow the determination of the SH signal strength, analytical throughput, and sorting efficiency at slower flow rates. This data, in turn, can be extrapolated to determine the performance at higher throughput speeds. Establishment of these performance parameters will allow integration of SHG into systems with faster throughputs.

Methods

SH Analysis of PSC-CMs in Flow Through a Microfluidic Channel

Figure 11:
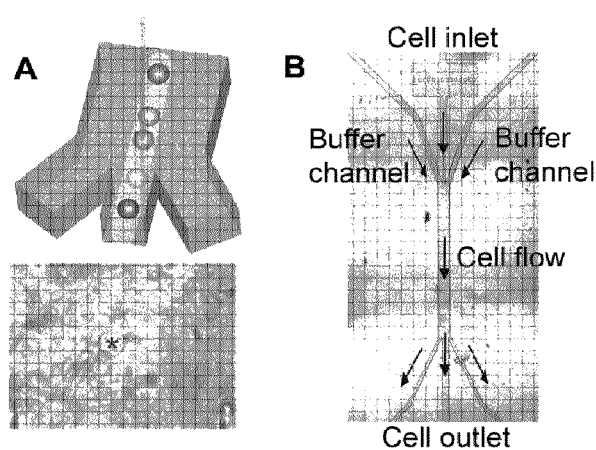
FIG. 11A is a Schematic of a three channel microfluidic device hydrodynamically focusing a stream of cells to the laser beam for spectral analysis. The image shows the overlap of a cell with the laser beam (*) positioned in the center channel.
FIG. 11B is a Brightfield image of the microfluidic device showing the sorting channels downstream for collecting two populations.

An optofluidic Raman spectroscopy cell sorter was developed by integrating Raman spectroscopic analysis of cells with multichannel microfluidic devices made of polydimethylsiloxane (PDMS) and mounted on 170 µm thick glass coverslips (FIG. 11A-B). The center, inlet channel (50×100 µm²) delivers a stream of cells into the device while the two buffer input channels hydrodynamically focus the cells into a cell probes cells as they flow past the beam.

Prior developed equivalent microdevices can be modified for this application using the desired parameters as described herein. In lieu of the tightly focused Gaussian beam geometry that was used in the Raman system, the SHG system can integrate the lightsheet illumination excitation design from Experiment B. By adjusting the flow rate (0.5-100 µmin) and the concentration of PSC-CM samples, typical throughputs of up to thousands of cells/sec can be achieved through the interrogation region of the microchannel. Signal strength as cells flow through the interrogation volume can be determined at different flow rates and laser powers. For example, a ~30 day post-differentiation PSC-CM sample can be prepared in suspension, fluorescently stained (α-actinin), and fixed. The optical system can be designed such that both two photon fluorescence and SH signals can be detected simultaneously from a cell passing through the excitation region by splitting the 465 nm SH signal and fluorescence signal with a dichroic beam splitter to two separate PMT detectors. This allows confirmation of the CM phenotype of each cell and the determination of SH signal intensity. Based on this SH intensity, one can extrapolate how signal strength behaves at high flow rates which we can be used to determine the maximum theoretical analytical throughput of an SHG cell sorter.

PSC-CMs can be tested at different stages of maturation (~9-40 day differentiation) to determine the feasibility of discriminating cells at different stages of their development under flow conditions through the microchannel.

Development of an All-Optical SHG-Activated Cell Sorter

Figure 12:
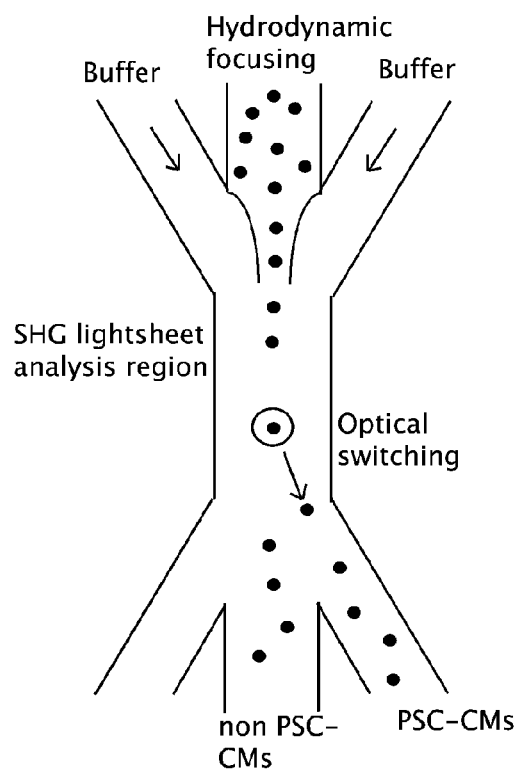
FIG. 12 is a schematic of an optical sorting based SH cell sorter for sorting PSC-CMs from PSCs and other non PSC-CMs. SHG region probes individual cells. SH signal triggers an optical switching downstream that deflects PSC-CMs into a separate channel from non PSC-CMs.

The Raman-based cell sorter described above used an all-optical approach for cell sorting. An advantage of an optical scheme is the overall simplicity of the design, and the relative speed at which cells can be sorted in a microflow based system. Based on their unique Raman signatures, cells were manipulated into adjacent channels for sorting and collection via an optical trap switching effect in which cells are physically moved by the optical forces of the laser beam. This was accomplished by using a galvanomirror to rapidly deflect the position of the laser beam trap to different adjacent channels. An SHG cell sorter can be designed to demonstrate sorting PSC-CMs. The sorting scheme can also integrate optical switching for fluorescence based microfluidic cell sorting. Although optical microflow cytometers have limited cell-sorting rates, this embodiment provides for a sorting system to as an SHG sorter. The advantages are: 1) it is a proven technology, 2) it has a range of sorting throughputs (~1000-300,000 cells/hour) and speeds (sub-ms to ms per cell) that are appropriate for our application and 3) cell manipulation via optical force switching is already tested. In this design (FIG. 12), a continuous microfluidic stream carries the cell to the Y-shape optical detection/sorting junction of the microfluidic device. Lateral hydrodynamic focusing flows align the cell suspension into a narrow stream in the middle of the microchannel for SH analysis in the lightsheet region. The flow is split into the waste and collection channels. Non-CM cells will move to the waste channel unless the SH signal from a PSC-CM activates the optical switch downstream, triggering a second laser ($\lambda$=1.06 µm, 5+ W) controlled by a high speed (GHz) acousto-optic modulator (AOM) to laterally displace the cell from its original flow stream to the collection channel by optical forces. The sorting laser will be loosely focused using a low 0.2 NA objective, allowing cells at different axial positions in the channel to be deflected. The optical forces (i.e., laser power and focusing) acting on the targeted PSC-CMs can be optimized under different flow rates. Custom electronic boards (National Instruments) and software (LabView) can be used to perform real time signal detection, thresholding, active AOM control, and overall system synchronization with a computer.

Determining Cell Viability and Sorting Accuracy

In another aspect, unstained live PSC-CMs (9-30 day postdifferentiation) can be used. The two cell populations are collected post-sort from both downstream channels and stained for both CM (e.g., α-actinin) and stem cell (e.g., Oct4) markers to quantify the accuracy of the sort. If needed, other markers, such as Islet 1 or Nkx2.5, in combination with the aforementioned markers, are used to further delineate more immature cells that may be present. Trypan blue dye exclusion can be used to determine for the post-sorted cells to determine whether the hydrodynamic focusing and laser exposure induce any cell damage.

In an alternative embodiment, additional channels are added. For example, although skeletal myocytes are not expected to be present in the cell population, additional optical channels can be added to the system to detect light scattering from the cells to eliminate, by size selection, skeletal myocytes, which are larger than PSC-CMs. Laser damage of the cells, either via the SHG excitation or the sorting laser, is not anticipated at the laser powers used given the extensive SHG and laser damage studies that have reported non-invasive, nondestructive analysis of cell and tissue dynamics at these power levels. In one aspect, additional more sensitive testing is provided. Although trypan blue dye exclusion is an adequate gross indicator of whether damage is occurring, it may lack the sensitivity to assess whether the laser has altered the cell. Additional experiments can be conducted to further assess potential laser damage. Sorted cells can be replated to assess longer-term cell viability in culture and cell viability assays (MTT, caspase 3) can be used. In one aspect, if the SHG excitation power needs to be reduced to further avoid damage, an electro-optic laser pulse picker can be used to reduce the average laser power (by reducing the repetition rate of the laser pulse train) while maintaining the peak intensity of each laser pulse, which is important for generating a strong SH signal. If needed, a lock-in detection scheme using a lock-in amplifier to detect the SH signal at the same frequency as the pulse picker frequency while eliminating the background signals can also be implemented to increase the detection sensitivity at low excitation laser power levels.

Without being bound by theory, in sum, the following quantitative results can be achieved. Experiment A will discriminate PSC-CMs from PSCs based on SH signal with >95% classification sensitivity and specificity, and discriminate PSC-CM populations that are separated by at least 10 post-differentiation days with classification sensitivity and specificity >80%.

Experiment B can demonstrate a system and method for functional light sheet excitation geometry for SH analysis of whole PSC-CM cells in suspension. Benchmark parameters include without limitation: min. Bessel beam scan rate of 1 kHz, min. optical dimensions of $10 \times 10$ $\mu m^2$ and demonstrate SH signal acquisition time of <=1 ms. For circular polarization, SH signal fluctuation for similar PSC-CMs should be <15% to allow for discrimination between populations at two differentiation time points. This % is estimated, and will vary depending on the mean intensity difference between the two populations.

Experiment C can demonstrate a system and method for a conservative, minimum SH analytical throughput of 500-1000 cells/sec (nonsorting throughput) and demonstrate sorting at a rate of 100 cells/sec (max. optical switching speed) in order to collect 100,000+ cells/hour. Additionally, the sorting accuracy will be: 0% PSCs in PSC-CM population. <10% PSC-CMs in PSC population and viability of PSC-CMs will be greater than 90% as determined by trypan blue method.

Unless otherwise defined, all technical and scientific terms used herein have the same meaning as commonly understood by one of ordinary skill in the art to which this invention belongs. All nucleotide sequences provided herein are presented in the 5' to 3' direction.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

The invention claimed is:

1. A method for sorting and isolating a stem-cell derived, stage-specific immature cardiomyocyte, comprising:
 (a) illuminating an incident light onto a plurality of stem-cell derived cells that comprise at least an undifferentiated cell and an immature cardiomyocyte possessing an intracellular noncentrosymmetric structure, wherein the immature cardiomyocyte generates second-harmonic light from the incident light;
 (b) identifying the stage of differentiation in the immature cardiomyocyte by detecting the intensity of the second-harmonic light generated by the immature cardiomyocyte; and
 (c) sorting and isolating the stage-specific immature cardiomyocyte identified in step (b), wherein the noncentrosymmetric structure is myosin.

2. The method of claim 1, wherein the immature cardiomyocyte is differentiated, in vitro, from a stem-cell wherein the duration of the differentiation is less than 180 days.

3. The system of claim 2, wherein the duration of the differentiation is less than 30 days.

4. The method of claim 2, wherein the stem-cell that produces the a stem-cell derived immature cardiomyocyte is of the group: an embryonic stem cell, an induced pluripotent stem cell, a multipotent stem cell, an oligopotent stem cell, or a unipotent stem cell.

5. The method of claim 1, wherein the incident light has a wavelength from about 700 nm to about 1500 nm.

6. The method of claim 1, wherein the incident light comprises pulses having a width of about 70 fs to about 10 ps.

7. The method of claim 1, wherein the incident light has a repetition rate from about 1 KHz to about 100 MHz.

8. The method of claim 1, wherein the cell is isolated in the absence of exogenous label or the cell is isolated in the absence of genetic modification of the cells.

9. The method of claim 8, wherein the exogenous label is a fluorescent label or a radioactive label.

10. The method of claim 1, further comprising suspending the cells in a medium prior to illuminating the incident light onto the cells.

11. The method of claim 10, wherein the medium comprises collagenase.

12. The method of claim 10, wherein the medium does not contain trypsin.

13. The method of claim 1, wherein the stem cell is a mammalian stem cell.

14. The method or population of claim 13, wherein the stem cell is of the group of a murine stem cell or a human stem cell.

15. The method of claim 1, wherein the stage of differentiation is identified by detecting low intensity second harmonic light.

16. The method of claim 1, wherein the stage of differentiation is identified by detecting high intensity second harmonic light.

* * * * *